United States Patent [19]

Matsuoka et al.

[11] Patent Number: 5,384,236
[45] Date of Patent: Jan. 24, 1995

[54] SILVER HALIDE COLOR PHOTOGRAPHIC MATERIAL

[75] Inventors: Koushin Matsuoka; Yasuhiro Shimada; Hiroyuki Yoneyama, all of Kanagawa, Japan

[73] Assignee: Fuji Photo Film Co., Ltd., Kanagawa, Japan

[21] Appl. No.: 257,189

[22] Filed: Jun. 8, 1994

[30] Foreign Application Priority Data

Jun. 8, 1993 [JP] Japan .................................. 5-163254

[51] Int. Cl.$^6$ .............................................. G03C 7/38
[52] U.S. Cl. .................... 430/558; 430/384; 430/385
[58] Field of Search ................ 430/558, 384, 385

[56] References Cited

U.S. PATENT DOCUMENTS

| | | | |
|---|---|---|---|
| 4,728,598 | 3/1988 | Bailey et al. | 430/387 |
| 4,818,672 | 4/1989 | Masukawa et al. | 430/558 |
| 4,873,183 | 10/1989 | Tachibana et al. | 430/550 |
| 5,256,526 | 10/1993 | Suzuki et al. | 430/384 |
| 5,270,153 | 12/1993 | Suzuki et al. | 430/558 |

FOREIGN PATENT DOCUMENTS

| | | |
|---|---|---|
| 0491197 | 6/1992 | European Pat. Off. |
| 0518238 | 12/1992 | European Pat. Off. |
| 0545300 | 6/1993 | European Pat. Off. |

*Primary Examiner*—Lee C. Wright
*Attorney, Agent, or Firm*—Sughrue, Mion, Zinn, Macpeak & Seas

[57] ABSTRACT

A silver halide color photographic material comprising a support having provided thereon at least one layer containing at least one cyan coupler represented by formula (I)

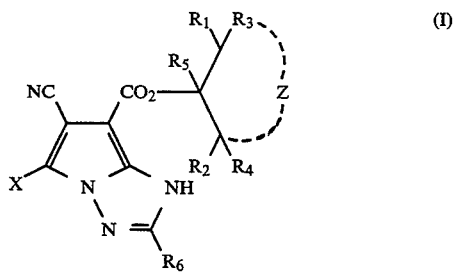

wherein
$R_1$ and $R_2$ each represent a substituent except methyl group;
$R_3$, $R_4$, $R_5$ and $R_6$ each represent a hydrogen atom or a substituent;
Z represents a non-metallic atom or a non-metallic atomic group necessary for forming a ring and the non-metallic atomic group of Z may optionally be substituted by substituent(s); and
X represents a hydrogen atom, or a group of splitting off from the formula by coupling reaction with an oxidation product of an aromatic primary amine color developing agent.

19 Claims, No Drawings

SILVER HALIDE COLOR PHOTOGRAPHIC MATERIAL

FIELD OF THE INVENTION

The present invention relates to a silver halide color photographic material, which, as the case may be, will be hereinafter referred to simply as a photographic material.

BACKGROUND OF THE INVENTION

It is well known that a silver halide color photographic material contains coupler(s) and that the coupler(s) in the material is/are reacted with an oxidation product of an aromatic primary amine color developing agent, that has been formed by oxidation with the exposed silver halide in the material as an oxidizing agent, to form a color image composed of indophenol, indoaniline, indamine, azomethine, phenoxazine, phenazine and the related dyes. In such a photographic system, subtractive color photography is used, and color images are formed of yellow, magenta and cyan dyes.

Of these, for producing cyan color images, phenol or naphthol couplers are generally used. However, since these couplers have unfavorable absorption in a green range, they have a serious problem that they noticeably lower the color reproducibility. Therefore, it is desired to overcome the problem.

As a means for overcoming the problem, heterocyclic compounds as described in U.S. Pat. Nos. 4,728,598 and 4,873,183 and European Patent 249,453A2 (corresponding to U.S. Pat. No. 4,818,672) have been proposed. However, these have a fatal problem that the coupling activity thereof is low. As couplers free from the problem, pyrroloazoles described in European Patent Laid-Open No. 0491197A1 (corresponding to U.S. Pat. No. 5,256,526) have been proposed. These couplers are excellent in point of the coupling activity of themselves and the color hue of the dyes to be formed therefrom. However, the pyrroloazotes disclosed in the patent had a problem that the color density of the dyes to be formed from them often fluctuates due to the fluctuation of the composition of the bleach-fixing solution (hereinafter referred to as "blix solution") to be used for processing the photographic materials containing the couplers. The fluctuation of the color density of the dyes formed was noticeable especially when the concentrations of thiosulfato ions and sulfito ions in the blix solution vary during continuous processing. The couplers had another problem with respect to the fastness of the color images to be formed therefrom in that the fastness of the image part having a relatively low color density is inferior to that of the image part having a high color density. For these reasons, it has been desired to improve the couplers in order to put them into practical use. In addition, the couplers had still another problem that they give a large cyan fog in the unexposed areas of the photographic materials during continuous processing. Given the situation, it has been desired to improve the couplers so as to overcome the problems.

SUMMARY OF THE INVENTION

One object of the present invention is to provide a silver halide color photographic material containing cyan coupler(s) having a high coupling activity to form dye(s) having an excellent color hue without fluctuation of the color density thereof to be caused by fluctuation of the composition of the blix solution used for processing the material.

Another object of the present invention is to provide a silver halide color photographic material containing cyan coupler(s) capable of forming color images where the fastness in the parts having a low color density is improved.

A further object of the present invention is to provide a silver halide color photographic material containing cyan coupler(s) of causing little cyan color fog in the non-exposed areas of the material during continuous processing.

The above-mentioned objects of the present invention have been attained by a silver halide color photographic material comprising a support having provided thereon at least one layer containing at least one cyan coupler represented by formula (I)

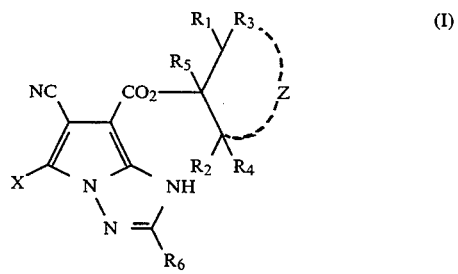

wherein
$R_1$ and $R_2$ each represent a substituent except methyl group;
$R_3$, $R_4$, $R_5$ and $R_6$ each represent a hydrogen atom or a substituent;
Z represents a non-metallic atom or a non-metallic atomic group necessary for forming a ring, the non-metallic atomic group of Z may optionally be substituted by substituent(s); and
X represents a hydrogen atom, or a group of splitting off from the formula by coupling reaction with an oxidation product of an aromatic primary amine color developing agent.

DETAILED DESCRIPTION OF THE INVENTION $R_1$, $R_2$, $R_3$, $R_4$, $R_5$, $R_6$ and X in formula (I) will be explained in detail hereunder.

Where the substituents as referred to herein contain an aliphatic moiety or aliphatic moieties, the moiety or moieties may be linear, branched or cyclic (e.g., cycloalkyl), saturated or unsaturated (e.g., alkenyl), and substituted or unsubstituted, unless otherwise specifically indicated. The aliphatic moiety is preferably an alkyl group.

Where the substituents as referred to herein contain an aryl moiety or aryl moieties, the moiety or moieties may be substituted or unsubstituted, and monocyclic (e.g., phenyl) or condensed-cyclic (e.g., naphthyl). The aryl moiety is preferably a phenyl group.

Where the substituents as referred to herein contain a heterocyclic moiety or heterocyclic moieties, the hereto atoms constituting the ring of the heterocyclic moiety may be chosen from among nitrogen, oxygen and sulfur atoms, the ring is preferably 5-membered to 8-membered, the carbon and nitrogen atoms on the ring may be substituted or unsubstituted, and the ring may be monocyclic or condensed-cyclic.

The number of carbon atoms of the substituent as referred to herein indicates the total number of the carbon atoms constituting the substituent.

$R_1$ and $R_2$ each represent a substituent except methyl group.

$R_1$ and $R_2$ include, for example, a halogen atom (e.g., chlorine, bromine), an aliphatic group (e.g., linear or branched alkyl, aralkyl, alkenyl, alkynyl, cycloalkyl or cycloalkenyl group having from 2 to 36 carbon atoms; precisely, such as ethyl, propyl, isopropyl, t-butyl, tridecyl, 2-methanesulfonylethyl, 3-(3-pentadecylphenoxy)propyl, 3-{4-{2-[4-(4-hydroxyphenylsulfonyl)phenoxy]-dodecanamido}phenyl}propyl, 2-ethoxytridecyl, trifluoromethyl, cyclopentyl, 3-(2,4-di-t-amylphenoxy)propyl), an aryl group (preferably having from 6 to 36 carbon atoms, e.g., phenyl, naphthyl, 4-hexadecoxyphenyl, 4-t-butylphenyl, 2,4-di-t-amylphenyl, 4-tetradecanamidophenyl, 3-(2,4-tert-amylphenoxyacetamido)phenyl), a heterocyclic group (e.g., 3-pyridyl, 2-furyl, 2-thienyl, 2-pyridyl, 2-pyrimidyl, 2-benzothiazolyl), an alkoxy group (preferably having from 1 to 30 carbon atoms, e.g., methoxy, ethoxy, 2-methoxyethoxy, 2-dodecyloxyethoxy, 2-methanesulfonylethoxy), an aryloxy group (preferably having from 6 to 30 carbon atoms, e.g., phenoxy, 2-methylphenoxy, 4-tert-butylphenoxy, 2,4-di-tert-amylphenoxy, 2-chlorophenoxy, 4-cyanophenoxy, 3-nitrophenoxy, 3-t-butyloxycarbamoylphenoxy, 3-methoxycarbamoylphenoxy), a heterocyclic-oxy group (e.g., 2-benzimidazolyloxy, 1-phenyltetrazol-5-oxy, 2-tetrahydropyranyloxy), an alkyl-, aryl- or heterocyclic-thio group (preferably having from 1 to 36 carbon atoms, e.g., methylthio, ethylthio, octylthio, tetradecylthio, 2-phenoxyethylthio, 3-phenoxypropylthio, 3-(4-tert-butylphenoxy)propylthio, phenylthio, 2-butoxy-5-tert-octylphenylthio, 3-pentadecylphenylthio, 2-carboxyphenylthio, 4-tetradecanamidophenylthio, 2-benzothiazolylthio, 2,4-di-phenoxy-1,3,4-triazol-6-thio, 2-pyridylthio), an alkyl-, aryl- or heterocyclic-acyloxy group (preferably having from 2 to 30 carbon atoms, e.g., acetoxy, hexadecanoyloxy), a carbamoyloxy group (preferably having from 1 to 30 carbon atoms, e.g., N-ethylcarbamoyloxy, N-phenylcarbamoyloxy), a silyloxy group (preferably having from 1 to 30 carbon atoms, e.g., trimethylsilyloxy, dibutylmethylsilyloxy), an alkyl- aryl- or heterocyclic-sulfonyloxy group (preferably having from 1 to 30 carbon atoms, e.g., dodecylsulfonyloxy), an acylamino group (preferably having from 2 to 30 carbon atoms, acetamido, benzamido, tetradecanamido, 2-(2,4-di-tert-amylphenoxyacetamido, 2-[4-(4-hydroxyphenylsulfonyl)phenoxy)]decanamido, isopentadecanamido, 2-(2,4-di-t-amylphenoxy)-butanamido, 4-(3-t-butyl-4-hydroxyphenoxy)-butanamido), an alkylamino group (preferably having from 1 to 30 carbon atoms, e.g., methylamino, butylamino, dodecylamino, dimethylamino, diethylamino, methylbutylamino), an arylamino group (preferably having from 6 to 30 carbon atoms, e.g., phenylamino, 2-chloroanilino, 2-chloro-5-tetradecanamidoanilino, N-acetylanilino, 2-chloro-5-[α-2-tert-butyl-4-hydroxyphenoxy)dodecylamido]anilino, 2-chloro-5-dodecyloxycarbonylanilino), an ureido group (preferably having from 2 to 30 carbon atoms, e.g., methylureido, phenylureido, N,N-dibutylureido, dimethylureido), a sulfamoylamino group (preferably having from 1 to 30 carbon atoms, e.g., N,N-dipropylsulfamoylamino, N-methyl-N-decylsulfamoylamino), an alkenyloxy group (preferably having from 2 to 30 carbon atoms, e.g., 2-propenyloxy), a formyl group, an alkyl-, aryl- or heterocyclic-acyl group (preferably having from 1 to 30 carbon atoms, e.g., acetyl, benzoyl, 2,4-di-tert-amylphenylacetyl, 3-phenylpropanoyl, 4-dodecyloxybenzoyl), an alkyl-, aryl- or heterocyclic-sulfonyl group (preferably having from 1 to 30 carbon atoms, e.g., methanesulfonyl, octanesulfonyl, benzenesulfonyl, toluenesulfonyl), an alkyl-, aryl- or heterocyclic-sulfinyl group (preferably having from 1 to 30 carbon atoms, e.g., octanesulfinyl, dodecylsulfinyl, phenylsulfinyl, 3-pentadecylphenylsulfinyl, 3-phenoxypropylsulfinyl), an alkyl-, aryl- or heterocyclic-oxycarbonyl group (preferably having from 2 to 30 carbon atoms, e.g. , methoxycarbonyl, butoxycarbonyl, dodecyloxycarbonyl, octadecyloxycarbonyl, phenyloxycarbonyl, 2-pentadecyloxycarbonyl), an alkyl-, aryl- or heterocyclic-oxycarbonylamino group (preferably having from 2 to 30 carbon atoms, e.g., methoxycarbonylamino, tetradecyloxycarbonylamino, phenoxycarbonylamino, 2,4-di-tert-butylphenoxycarbonylamino), an alkyl-, aryl- or heterocyclic-sulfonamido group (preferably having from 1 to 30 carbon atoms, e.g., methanesulfonamido, hexadecansulfonamido, benzenesulfonamido, p-toluenesulfonamido, octadecanesulfonamido, 2-methoxy-5-tert-butylbenzenesulfonamido), a carbamoyl group (preferably having from 1 to 30 carbon atoms, e.g., N-ethylcarbamoyl, N,N-dibutylcarbamoyl, N-(2-docecyloxyethyl)carbamoyl, N-methyl-N-dodecylcarbamoyl, N-[3-(2,4-di-tert-amylphenoxy)propyl]carbamoyl), a sulfamoyl group (preferably having from 1 to 30 carbon atoms, e.g., N-ethylsulfamoyl, N,N-dipropylsulfamoyl, N-(2-dodecyloxyethyl)sulfamoyl, N-ethyl-N-dodecylsulfamoyl, N,N-diethylsulfamoyl), a phosphonyl group (preferably having from 1 to 30 carbon atoms, e.g., phenoxyphosphonyl, octyloxyphosphonyl, phenylphosphonyl), a sulfamido group (preferably having from 1 to 30 carbon atoms, e.g., dipropylsulfamoylamino), an imido group (preferably having from 1 to 30 carbon atoms, e.g., N-succinimido, hydantoinyl, N-phthalimido, 3-octadecenylsuccinimido), an azolyl group (e.g., imidazolyl, pyrazolyl, 3-chloro-pyrazol-1-yl, triazolyl), an alkyl- or aryl-substituted silyl group (preferably having 1 to 36 carbon atoms, e.g., trimethylsilyl, t-butyldiphenylsilyl), a hydroxyl group, a cyano group, a carboxyl group, a nitro group, a sulfo group, and an unsubstituted amino group.

$R_1$ and $R_2$ each are preferably an aliphatic group having from 2 to 30 carbon atoms, an aryl group having from 6 to 30 carbon atoms, an alkoxy group having from 1 to 30 carbon atoms, an aryloxy group having from 6 to 30 carbon atoms, a halogen atom, an alkyl- or aryl-oxycarbonyl group, a carbamoyl group, or an alkyl- or aryl-substituted silyl group.

More preferably, $R_1$ and $R_2$ each are an aliphatic group having from 2 to 30 carbon atoms, an aryl group having from 6 to 30 carbon atoms, an alkoxy group having from 1 to 30 carbon atoms, or an aryloxy group having from 6 to 30 carbon atoms. Especially preferably, they each are a branched alkyl group having from 3 to 30 carbon atoms. $R_1$ and $R_2$ may be the same or different, and they may be substituted by one or more substituents such as those mentioned hereinabove.

$R_3$, $R_4$, $R_5$ and $R_6$ each represent a hydrogen atom or a substituent. The substituents of $R_3$, $R_4$, $R_5$ and $R_6$ include a methyl group and those mentioned hereinabove for $R_1$ and $R_2$.

$R_3$, $R_4$ and $R_5$ each are preferably a hydrogen atom, an alkyl group having from 1 to 30 carbon atoms, an aryl group, an alkoxy group, an aryloxy group, a halogen atom, or a group that is bonded to the formula via an ester group, an amido group or a silicon atom. The group bonded to the formula via an ester group includes an alkyl-, aryl- or heterocyclic-oxycarbonyl group. The group bonded to the formula via an amido group includes a carbamoyl group. The group bonded to the formula via an silicon atom includes an alkyl- or aryl-substituted silyl group. More preferably, $R_3$, $R_4$ and $R_5$ each are a hydrogen atom, or an alkyl, aryl, alkoxy or aryloxy group having from 1 to 30 carbon atoms. Especially preferably, they are hydrogen atoms. $R_3$, $R_4$ and $R_5$ may be the same or different, and they may be substituted by one or more substituents such as those mentioned hereinabove for $R_3$ to $R_6$.

$R_6$ is preferably an alkyl group, an aryl group, a heterocyclic group, a carbamoyl group, an acylamino group, or an ureido group. More preferably, it is an aryl group. Especially preferably, it is an aryl group having at least a substituent at its ortho-position.

$R_6$ is more preferably represented by the following formula

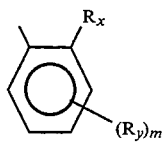

where $R_x$ and $R_y$ each represent a substituent that may be chosen from among the substituents of $R_3$ to $R_6$; and m represents an integer of from 0 to 4.

The substituent $R_x$ in the ortho-position is preferably a halogen atom, or a group that bonds to the phenyl nucleus via a hydrogen bond-accepting atom such as oxygen, nitrogen or sulfur atom, or a group containing such hydrogen bond-accepting atom(s) (e.g., methoxycarbonylmethyl, chloromethyl, methylthiomethyl, 2-N-methylpyrrole). More preferably, it is a group that bonds to the phenyl nucleus via an oxygen atom. Especially preferably, it is an alkoxy group having from 1 to 40 carbon atoms, or an aryloxy group having from 6 to 46 carbon atoms.

The compounds of the present invention include stereoisomers with respect to the substituents $R_1$ to $R_5$. Where the compounds of the present invention are used, either mixtures of such isomers or single isomers may be used.

In formula (I), Z represents an atom or an atomic group necessary for forming a 4-membered to 12-membered ring, preferably a 5-, 6-, 7- or 8-membered ring, along with the carbon atoms to which it is bonded. The divalent group Z which forms such a ring may be a divalent amino group, an ether bond, a thioether bond, an alkylene group, an alkenylene group, an-imino group, a sulfonyl group, or a carbonyl group, or a combination of two or more of them. The divalent amino group as Z is represented by

wherein R represents a hydrogen atom, an alkyl group or an aryl group. These may have one or more substituents such as those mentioned hereinabove for $R_3$ to $R_6$. The divalent group of Z which forms such a ring is preferably a divalent amino group, an ether bond, a thioether bond, an alkylene group, an alkenylene group, or an imino group. More preferably, it is an alkylene group or an alkenylene group. Most preferably, it is an alkylene group.

The ring to be formed by Z includes a cyclobutane ring, a cyclopentane ring, a cyclohexane ring, a cyclohexene ring, a 1,4-cyclohexadiene ring, a cycloheptane ring, a cyclooctane ring, an oxane ring, a piperidine ring, a 1,3-dioxane ring, a sulfolane ring and a thiane ring. The ring to be formed by Z is preferably a saturated, 6-membered carbon ring.

In formula (I), the moiety of:

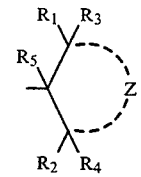

is preferably represented by the following formula:

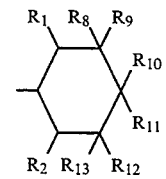

wherein $R_8$ to $R_{13}$ each represent a hydrogen atom or a substituent. As examples of the substituent, those mentioned hereinabove for $R_3$ to $R_6$ are referred to.

In formula (I), X represents a hydrogen atom or a group of splitting off from the formula when the coupler is reacted with an oxidation product of an aromatic primary amine color developing agent (the group is hereinafter simply referred to as a split-off group). As the split-off group, there are mentioned, for example, a halogen atom, an alkoxy group, an aryloxy group, a heterocyclic-oxy group, an alkyl-, aryl- or heterocyclic-acyloxy group, an alkyl-, aryl- or heterocyclic-sulfonyloxy group, a dialkyl- or diaryl-phosphonoxy group, a dialkyl- or diaryl-phosphinoxy group, an alkoxycarbonyloxy group, an aryloxycarbonyloxy group, a heterocyclic-oxycarbonyloxy group, an alkyl-, aryl- or heterocyclic-sulfonyl group, an alkyl-, aryl- or heterocyclic-sulfinyl group, an alkyl-, aryl- or heterocyclic-carbonyl group, an alkyl-, aryl- or heterocyclic-acylamino group, an alkyl-, aryl- or heterocyclic-sulfonamido group, a carbamoylamino group, an alkyl-, aryl- or heterocyclic-thio group, an imido group, an arylazo group, and a 5-membered or 6-membered, nitrogen-containing heterocyclic group that bonds to the coupling position of the formula via its nitrogen atom. The alkyl, aryl and heterocyclic moieties in these split-off groups may be substituted by one or more substituents such as those mentioned hereinabove for $R_3$ to $R_6$. Where the moieties have two or more substituents, the substituents may be the same or different and they may have one or more substituents such as those mentioned hereinabove for $R_3$ to $R_6$.

More precisely, the split-off group includes a halogen atom (e.g., fluorine, chlorine, bromine), an alkoxy group (preferably having from 1 to 30 carbon atoms, e.g., ethoxy, dodecyloxy, methoxyethylcarbamoylmethoxy, carboxypropyloxy, methylsulfonylethoxy, ethoxycarbonylmethoxy), an aryloxy group (preferably having from 6 to 36 carbon atoms, e.g., 4-methylphenoxy, 4-chlorophenoxy, 4-methoxyphenoxy, 4-carboxyphenoxy, 3-ethoxycarboxyphenoxy, 3-acetylaminophenoxy, 2-carboxyphenoxy), a heterocyclic-oxy group (preferably having from 1 to 36 carbon atoms, e.g., 5-phenyltetrazolyloxy, 2-benzothiazolyloxy), an alkyl-, aryl- or heterocyclic-acyloxy group (preferably having from 2 to 30 carbon atoms, e.g., acetoxy, tetradecanoyloxy, benzoyloxy), an alkyl-, aryl- or heterocyclic-sulfonyloxy group (preferably having from 1 to 30 carbon atoms, e.g., methanesulfonyloxy, toluenesulfonyloxy), a dialkyl- or diarylphosphonoxy group (preferably having from 1 to 30 carbon atoms, e.g., diethylphosphonoxy, diphenylphosphonoxy), a dialkyl- or diaryl-phosphinoxy group (preferably having from 1 to 30 carbon atoms, e.g., dimethylphosphinoxy), a heterocyclic-oxycarbonyloxy group (e.g., 5-phenyltetrazoiyloxycarbonyloxy, 2-benzothiazolyloxycarbonyloxy), an alkyl-, aryl- or heterocyclic-sulfonyl group (preferably having from 1 to 30 carbon atoms, e.g., toluenesulfonyl, methanesulfonyl, tetrazolylsulfonyl), an alkyl-, aryl- or heterocyclic-sulfinyl group (preferably having from 1 to 30 carbon atoms, e.g., phenylsulfinyl, i-propylsulfinyl, tetrazolylsulfinyl), an alkyl-, aryl- or heterocyclic-carbonyl group (e.g., acetyl, benzoyl, tetrazolylcarbonyl), an alkyl-, aryl- or heterocyclic-acylamino group (preferably having from 2 to 30 carbon atoms, e.g., dichloroacetylamino, heptafluorobutyrylamino), an alkyl-, aryl- or heterocyclic-sulfonamido group (preferably having from 1 to 30 carbon atoms, e.g., methanesulfonamido, trifluoromethanesulfonamido, p-toluenesulfonamido), an alkoxycarbonyloxy group (preferably having from 2 to 30 carbon atoms, e.g., ethoxycarbonyloxy, benzyloxycarbonyloxy), an aryloxycarbonyloxy group (preferably having from 7 to 36 carbon atoms, e.g., phenoxycarbonyloxy), an alkyl-, aryl- or heterocyclic-thio group (preferably having from 1 to 36 carbon atoms, e.g., ethylthio, 2-carboxyethylthio, dodecylthio, 1-carboxydodecylthio, phenylthio, perfluorophenylthio, 2-butoxy-5-t-octylphenylthio, tetrazolylthio), a carbamoylamino group (preferably having from 1 to 30 carbon atoms, e.g., N-methylcarbamoylamino, N-phenylcarbamoylamino), a 5-membered or 6-membered, nitrogen-containing heterocyclic group that bonds to the coupling position of the formula via its nitrogen atom (preferably having from 1 to 36 carbon atoms, e.g., imidazolyl, pyrazolyl, triazolyl, tetrazolyl, 1,2-dihydro-2-oxo-1-pyridyl), an imido group (preferably having from 1 to 30 carbon atoms, e.g., succinimido, hydantoinyl), and an arylazo group (preferably having from 6 to 36 carbon atoms, e.g., phenylazo, 4-methoxyphenylazo). As a matter of course, the split-off group may further be substituted by one or more substituents, such as those previously mentioned for $R_3$ to $R_6$. As a split-off group that bonds to the formula via a carbon atom, there are mentioned bis-type couplers to be obtained by condensation of 4-equivalent couplers with aldehydes or ketones. The split-off group of the present invention may contain a photographically useful group such as, for example, a development inhibitor or a development accelerator.

Preferably, X is a hydrogen atom, a halogen atom, an alkoxy group, an aryloxy group, an alkyl- or aryl-thio group, and a 5-membered or 6-membered nitrogen-containing heterocyclic group that bonds to the coupling-active position in the formula via a nitrogen atom. More preferably, it is a hydrogen atom or a halogen atom. Especially preferably, it is a chlorine atom.

Cyan couplers of formula (I) may be dimers or higher polymers in which the group(s) of $R_1$, $R_2$, $R_3$, $R_4$, $R_5$, $R_6$ and/or X are/is divalent group(s) to be bonded to dimer(s) or higher polymer(s) or to high molecular chain(s) to form homopolymers or copolymers. Such homopolymers or copolymers in which the group(s) is/are bonded to high molecular chain(s) are typically homopolymers or copolymers of addition-polymerizing ethylenic unsaturated compounds having cyan coupler residue(s) of formula (I). In these cases, the homopolymers or copolymers each may have one or more cyan coloring repeating units each having a cyan coupler residue of formula (I) in the polymer molecule and may contain one or more non-coloring ethylenic monomers as comonomer components to be copolymers. The cyan coloring repeating unit having a cyan coupler residue of formula (I) is preferably represented by the following formula (P):

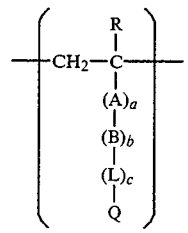

where R represents a hydrogen atom, an alkyl group having from 1 to 4 carbon atoms, or a chlorine atom;

A represents —CONH—, —COO—, or a substituted or unsubstituted phenylene group;

B represents a substituted or unsubstituted alkylene having from 1 to 30 carbon atoms, phenylene having from 6 to 36 carbon atoms or aralkylene group having from 7 to 37 carbon atoms;

L represents —CONH—, —NHCONH—, —NHCOO—, —NHCO—, —OCONH—, —NH—, —COO—, —OCO—, —CO—, —O—, —S—, —SO$_2$—, —NHSO$_2$—, or —SO$_2$NH—;

a, b and c each represent 0 or 1; and

Q represent a cyan coupler residue derived from a compound of formula (I) by removing a hydrogen atom from the group of $R_1$, $R_2$, $R_3$, $R_4$, $R_5$, $R_6$ or X in the respective formula.

As the polymers, preferred are copolymers comprising cyan coupler units of coloring monomers of formula (I) and non-coloring ethylenic monomers which do not couple with an oxidation product of an aromatic primary amine developing agent.

As non-coloring ethylenic monomers which do not couple with an oxidation product of an aromatic primary amine developing agent, for example, mentioned are acrylic acid, α-chloroacrylic acid, α-alkylacrylic acids (e.g., methacrylic acid) and amides or esters to be derived from these acrylic acids (e.g., acrylamide, methacrylamide, n-butylacrylamide, t-butylacrylamide, diacetylacrylamide, methyl acrylate, ethyl acrylate, n-propyl acrylate, n-butyl acrylate, t-butyl acrylate, iso-butyl acrylate, 2-ethylhexyl acrylate, n-octyl acrylate, lauryl acrylate, methyl methacrylate, ethyl methacrylate, n-butyl methacrylate, β-hydroxy methacrylate), vinyl esters (e.g., vinyl acetate, vinyl propionate, vinyl laurate), acrylonitrile, methacrylonitrile, aromatic vinyl compounds (e.g., styrene and derivatives thereof, such as vinyl toluene, divinylbenzene, vinylacetophenone and sulfoethylene), iraconic acid, citraconic acid, crotonic acid, vinylidene chloride, vinyl alkyl ethers (e.g., vinyl ethyl ether), maleates, N-vinyl-2-pyrrolidone, -N-vinylpyridine, and 2- and 4-vinylpyridines.

Of these, especially preferred are acrylates, methacrylates and maleates. In the present invention, the copolymers may contain two or more different non-coloring ethylenic monomers. For instance, mentioned are combination of methyl acrylate and butyl acrylate, combination of butyl acrylate and styrene, combination of butyl methacrylate and methacrylic acid, and combination of methyl acrylate and diacetoneacrylamide.

As well known in the field of polymer couplers, ethylenic unsaturated comonomers to be copolymerized with vinyl monomers corresponding to the above-mentioned formula (I) are so selected that the physical and/or chemical properties of the copolymers to be formed therefrom, such as the solubility of them, the compatibility of them with binders of photographic compositions such as gelatin, the flexibility of them as well as the thermal stability of them are favorably influenced by the selected comonomers.

For incorporating the couplers of the present invention into silver halide photographic materials, preferably into the red-sensitive silver halide emulsion layers of them, it is preferred that the couplers are in the form of so-called coupler-in-emulsion type ones. For this purpose, it is preferred that the total carbon number in the substituent $R_6$ is from 1 to 50, more preferably from 4 to 30, especially preferably from 7 to 20. The total carbon number in the alkoxy moiety in the ester part in the couplers of the present invention is preferably from 3 to 50, more preferably from 4 to 30, especially preferably from 6 to 20.

Next, specific examples of the couplers of the present invention are mentioned below, which, however, are not intended to restrict the scope of the present invention.

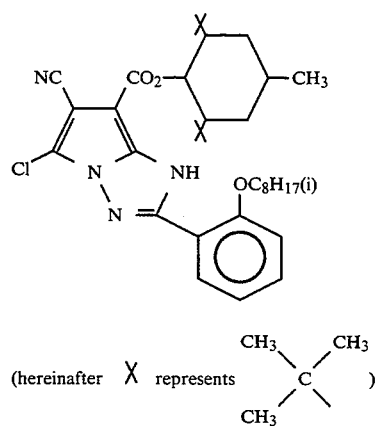

(1)

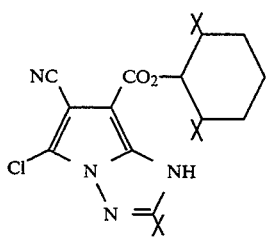

(2)

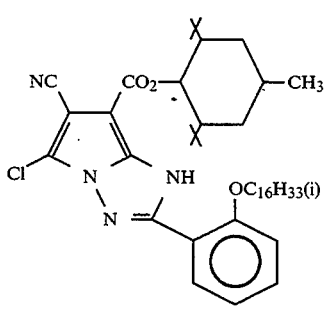

(3)

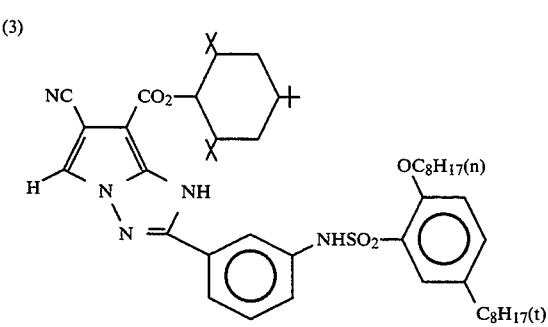

(4)

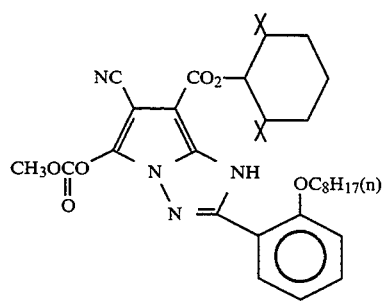

(5)

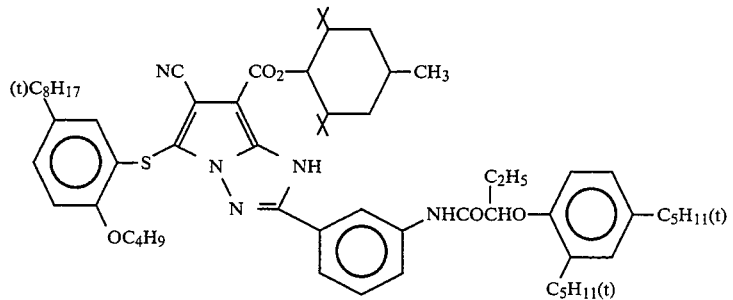
(6)
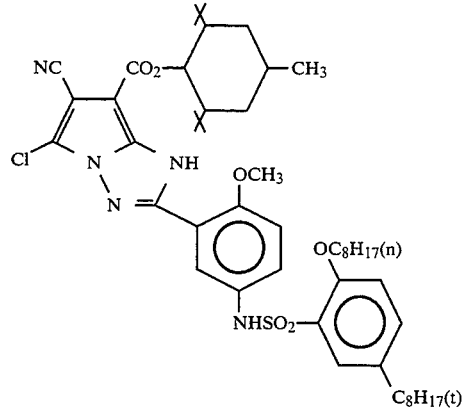
(7)
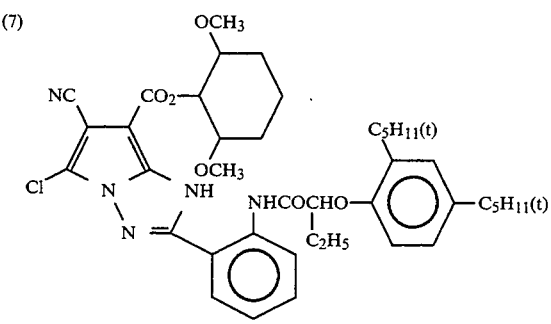
(8)
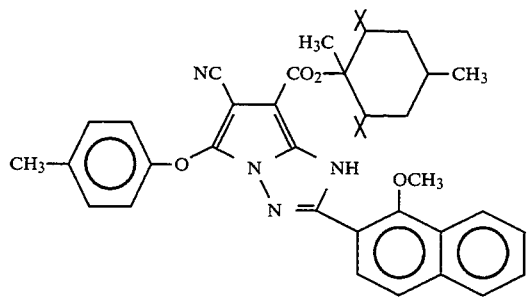
(9)
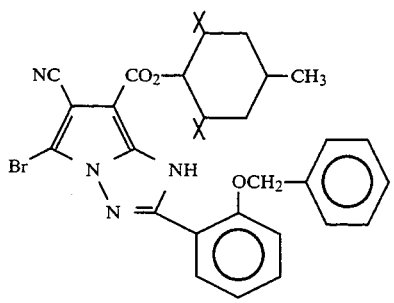
(10)
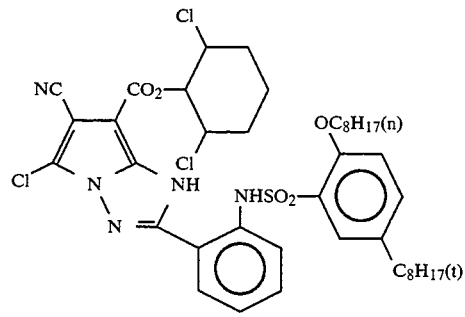
(11)

-continued
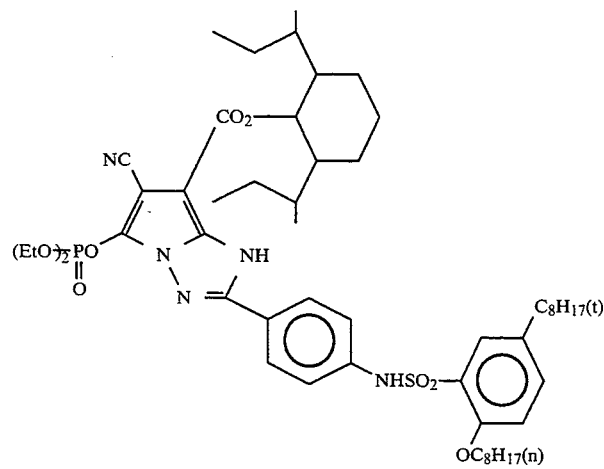
(12)
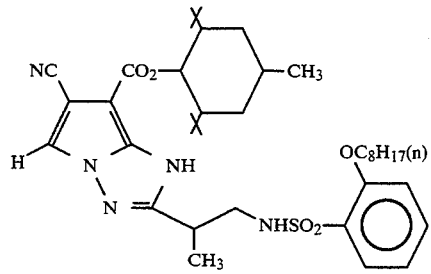
(13)
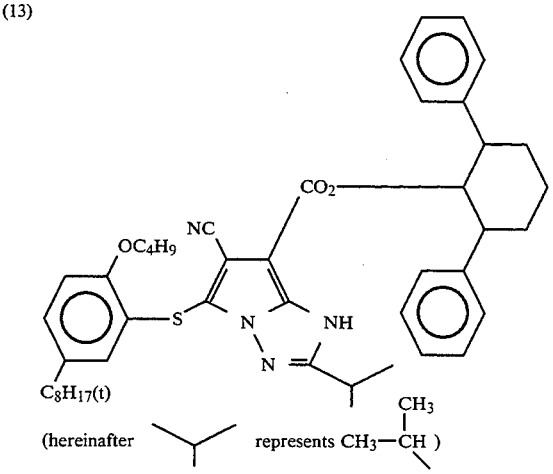
(14)
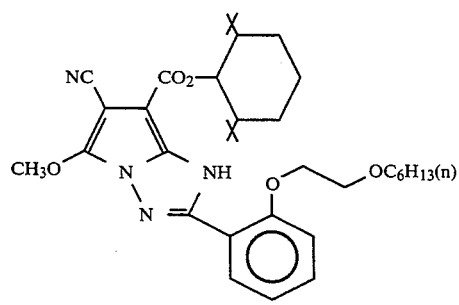
(15)

-continued
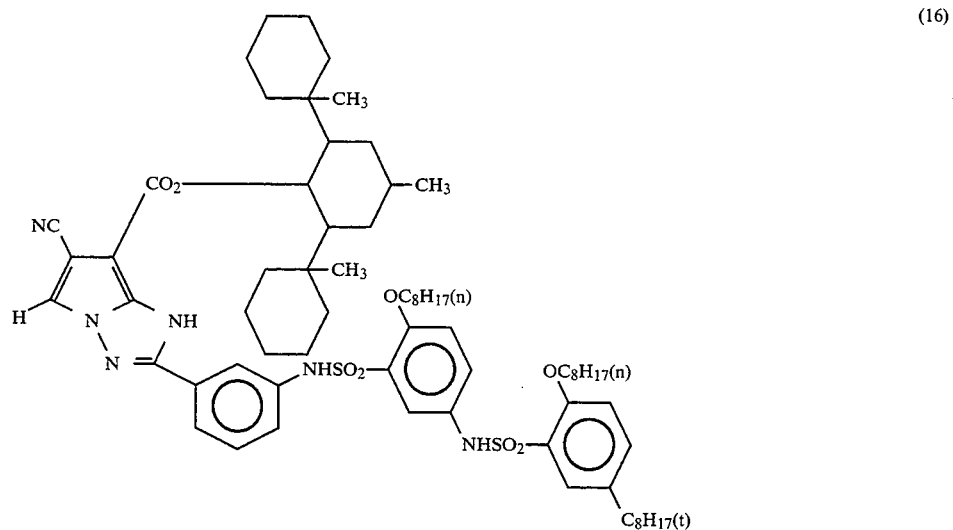
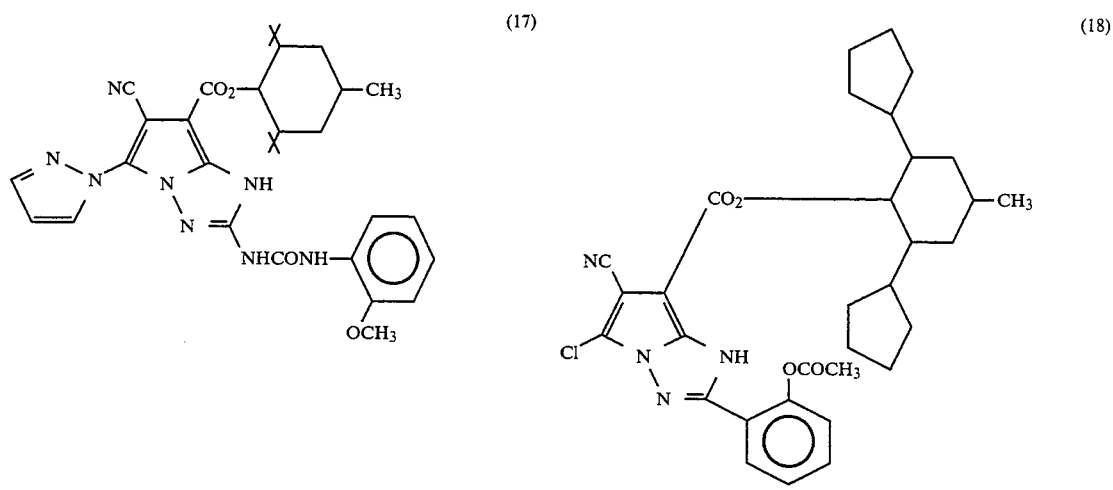
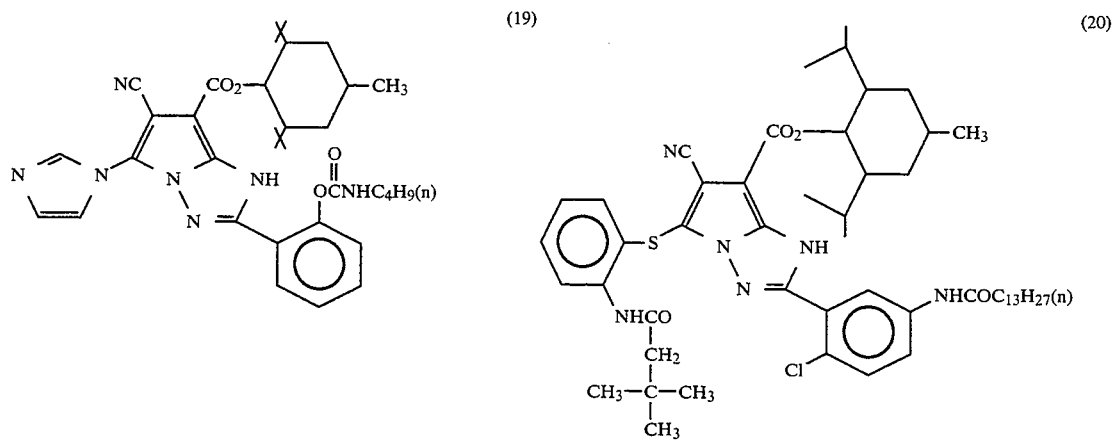

-continued
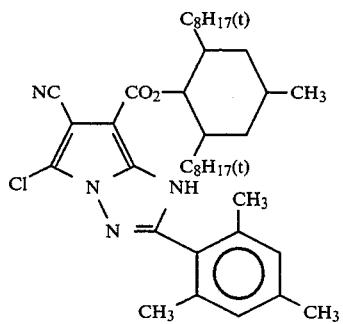
(21)
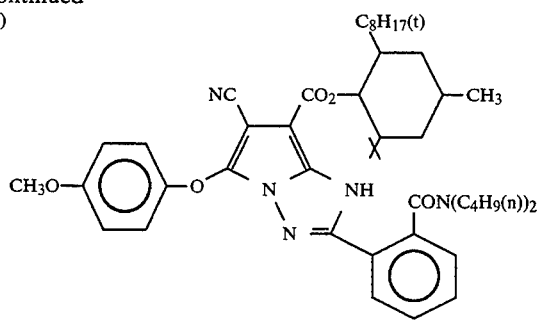
(22)
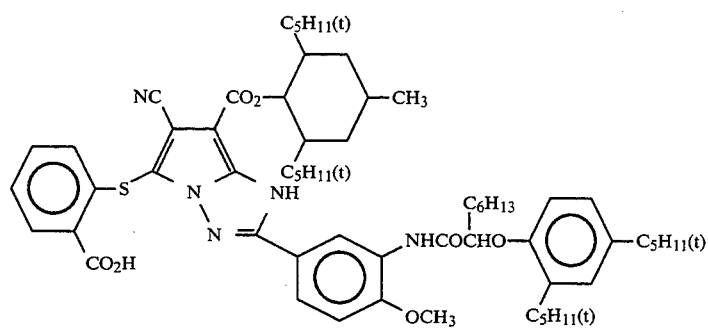
(23)
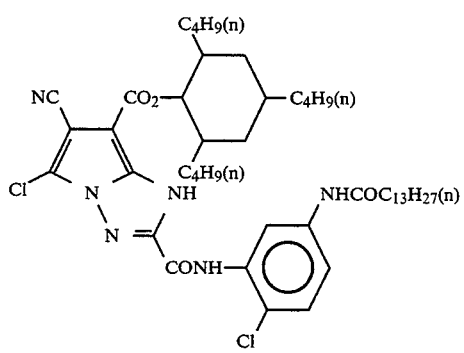
(24)
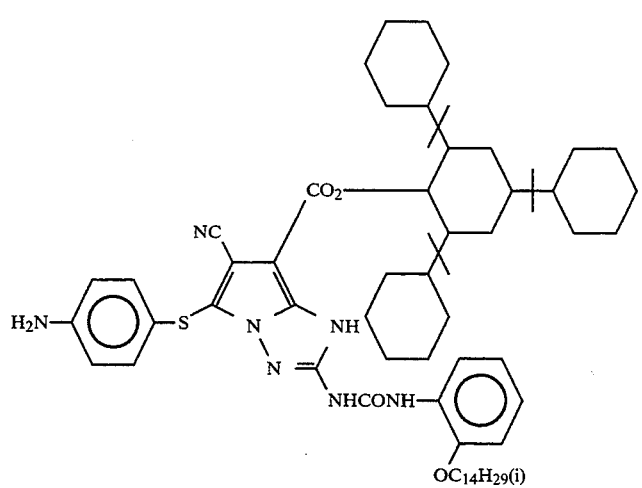
(25)

-continued
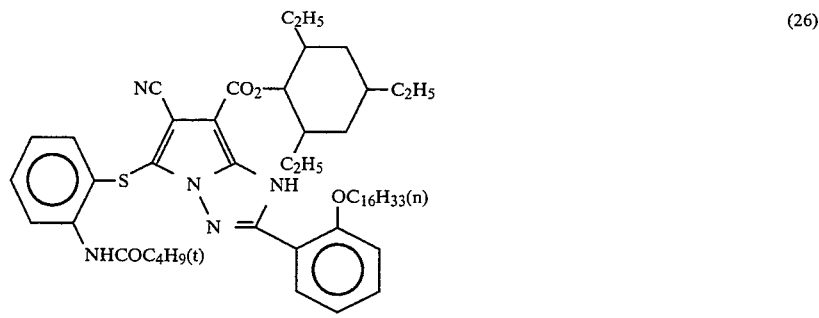 (26)
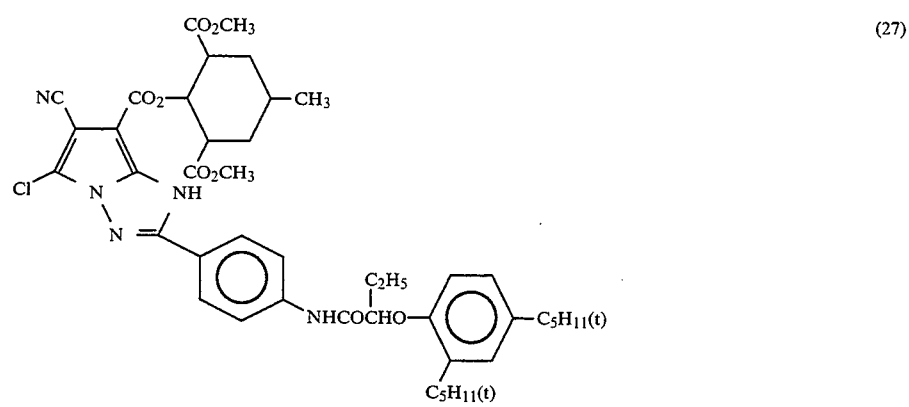 (27)
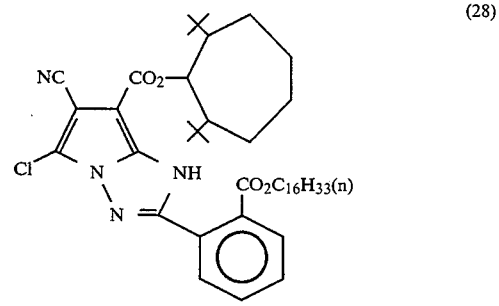 (28)
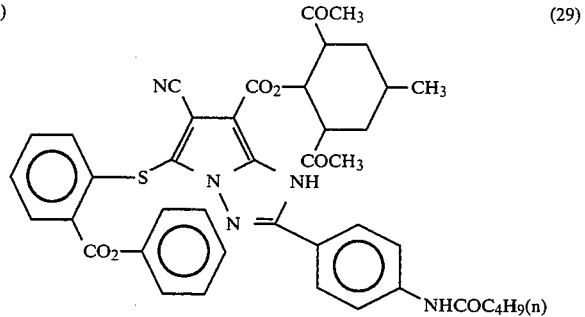 (29)
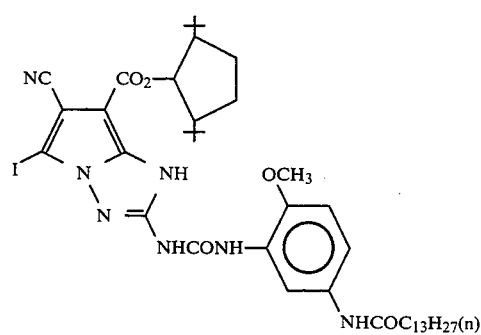 (30)
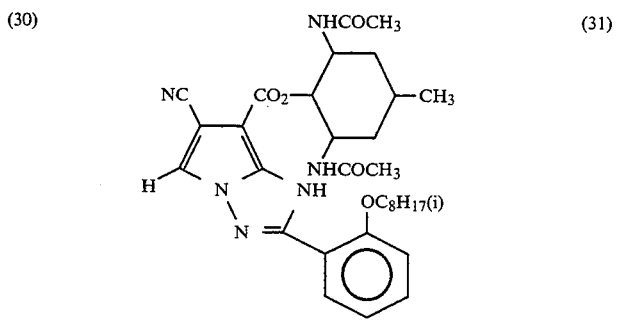 (31)

-continued
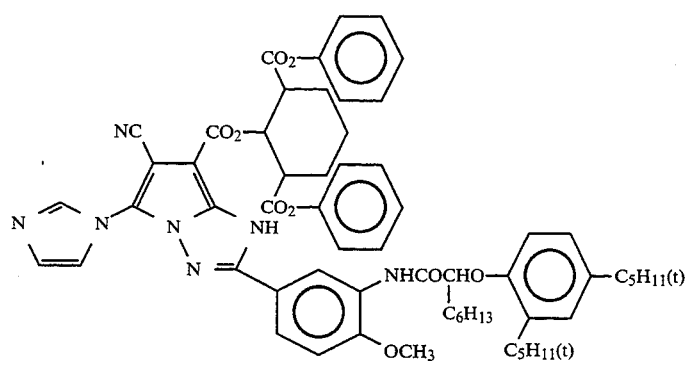 (32)
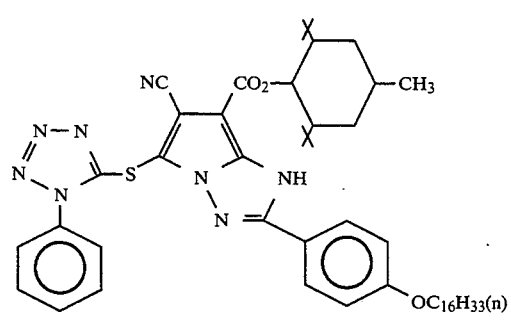 (33)
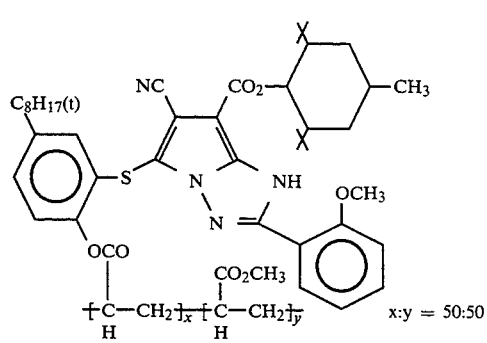 (34)
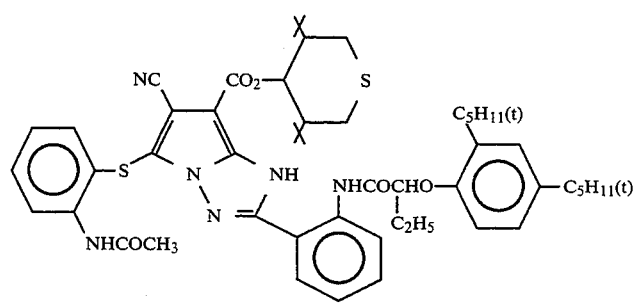 (35)
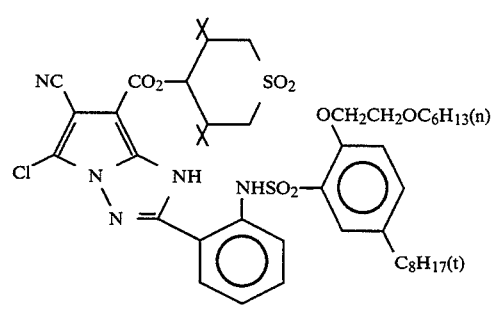 (36)
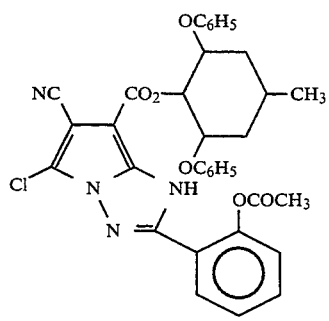 (37)

-continued
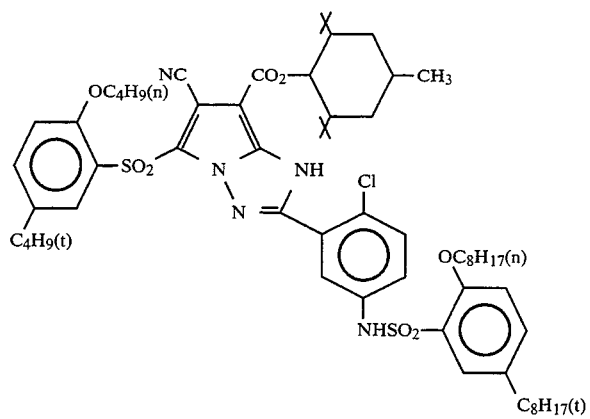
(38)
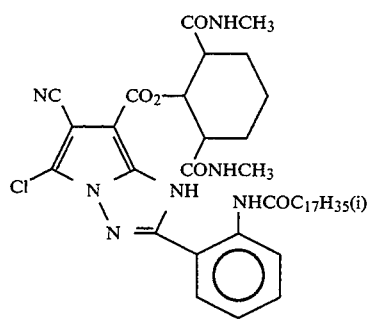
(39)
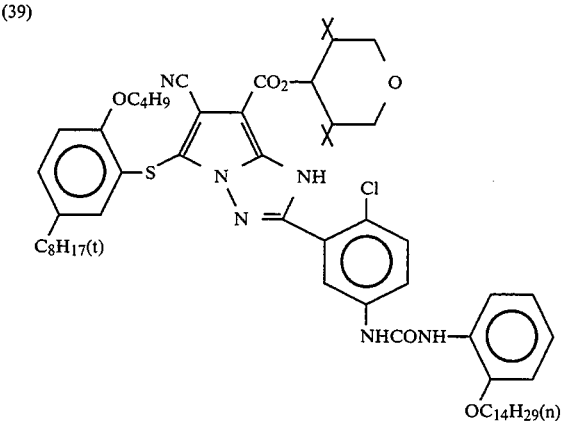
(40)
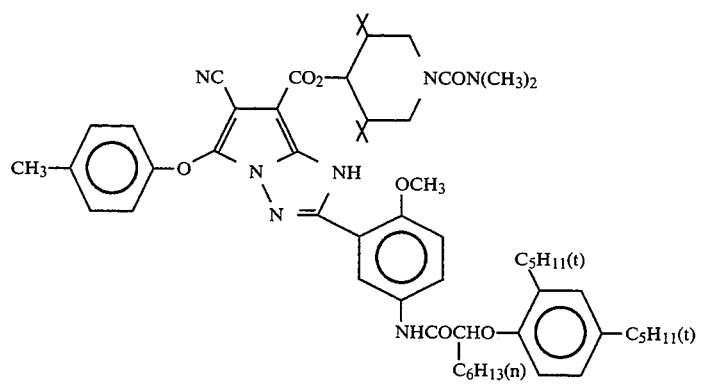
(41)
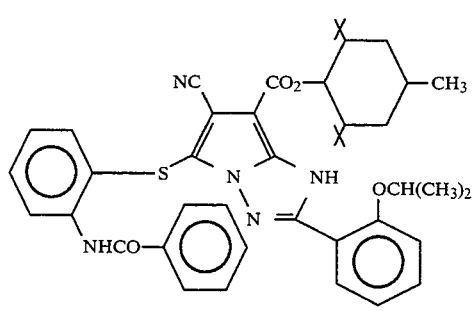
(42)
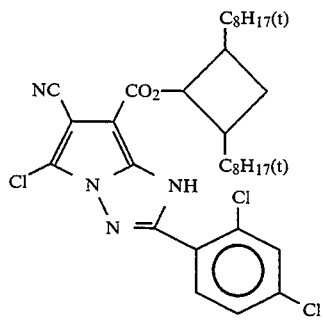
(43)

-continued
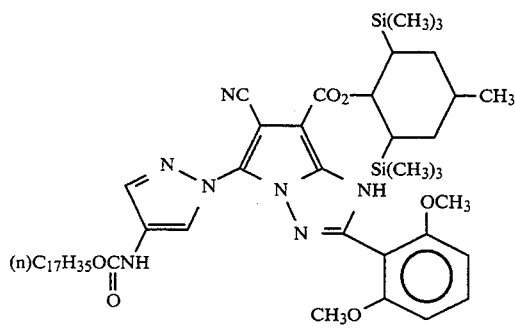  (44)
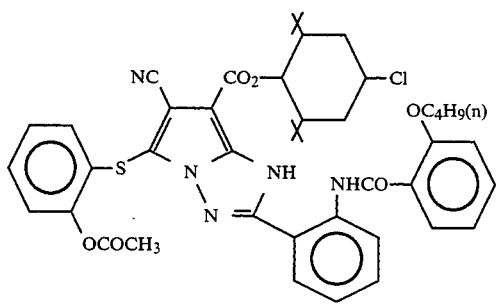  (45)
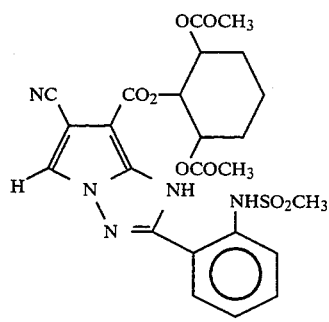  (46)
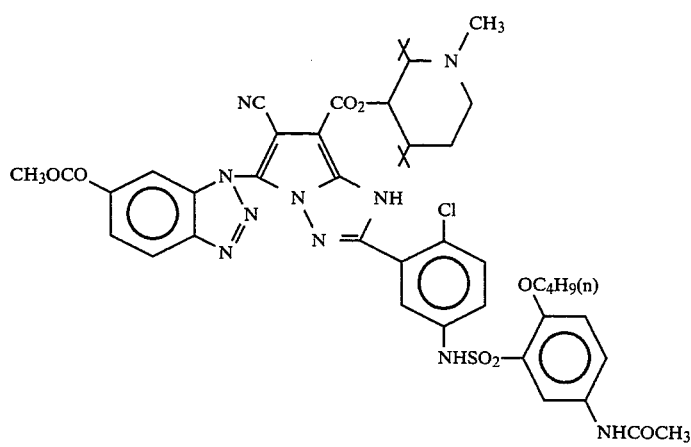  (47)
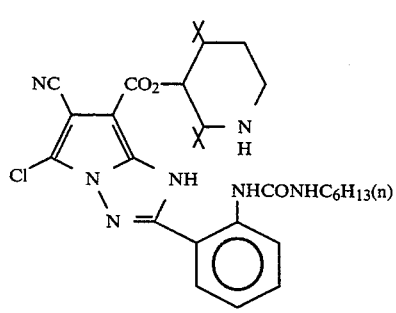  (48)
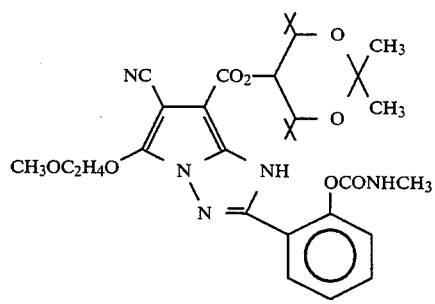  (49)
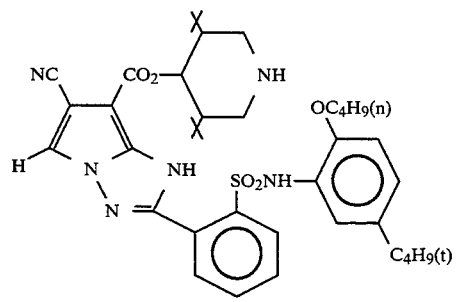  (50)
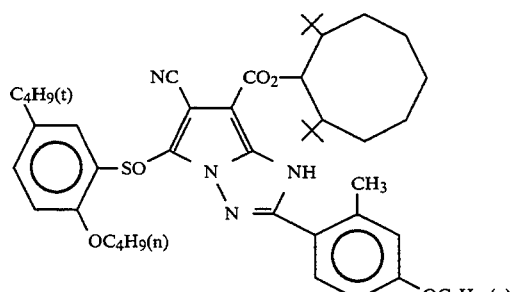  (51)

-continued
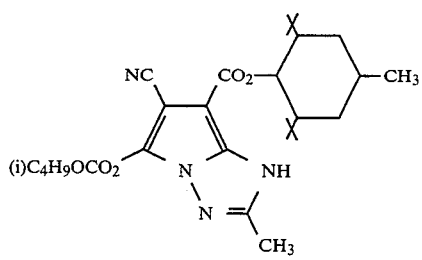 (52)
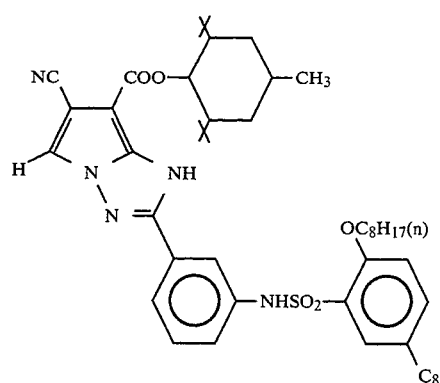 (53)
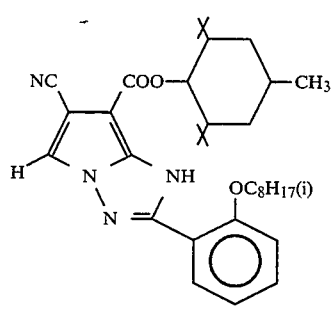 (54)
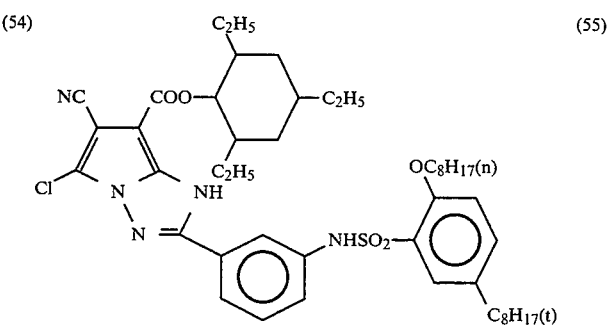 (55)
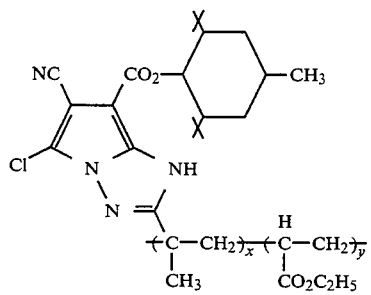 (56)
x:y = 50:50
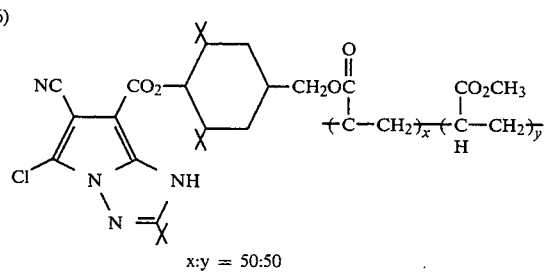 (57)
x:y = 50:50
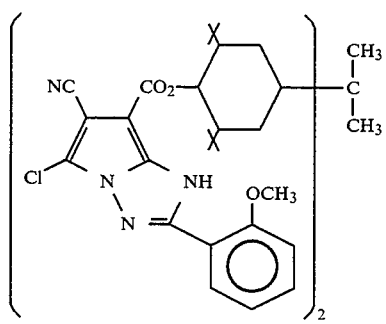 (58)
The production of the compounds of the present invention will be mentioned below.
A general method for producing the compounds of the present invention may be represented by the following reaction scheme:

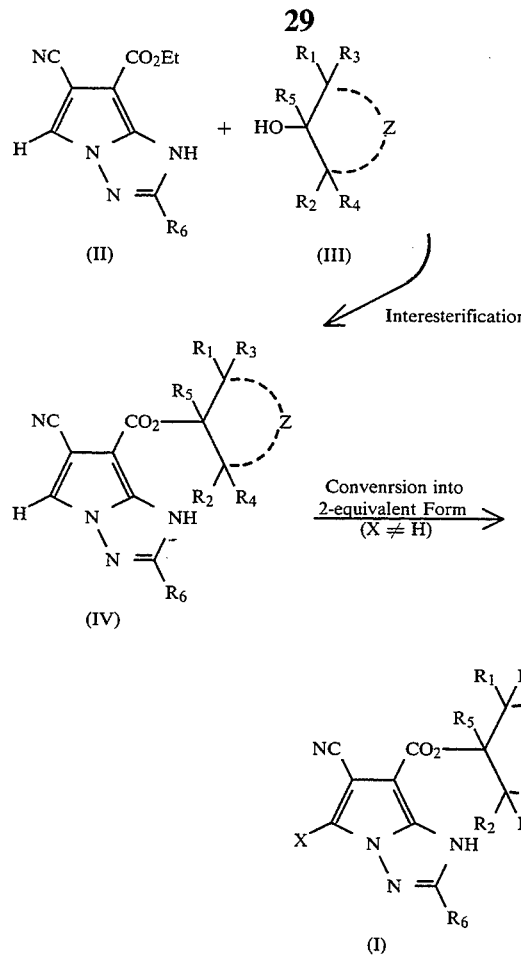

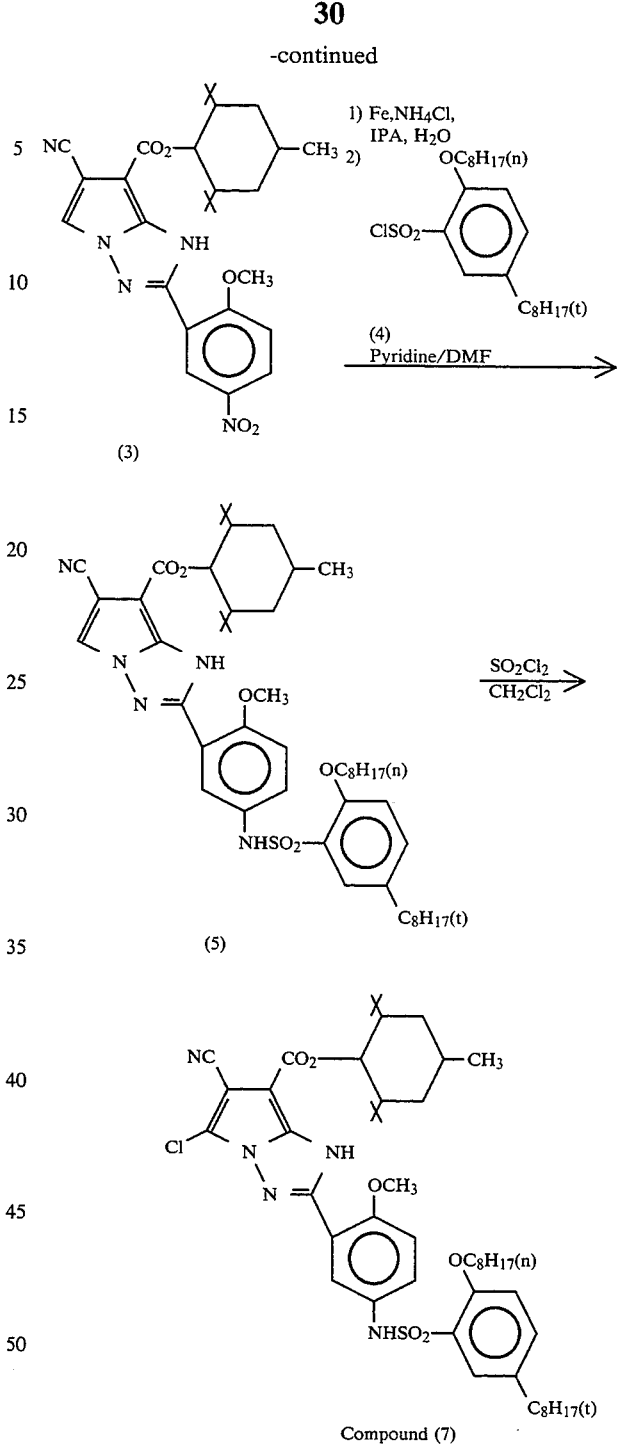

Compounds of formula (II) may be produced in accordance with the method described in European Patent Laid-Open No. 0491197A1 (corresponding to U.S. Pat. No. 5,256,526). The interesterification and the subsequent conversion into the 2-equivalent form (I) may also be effected in accordance with the method described in the same patent publication.

Next, some production examples of producing typical compounds of the present invention are mentioned below.

PRODUCTION EXAMPLE 1

Production of Compound (7)

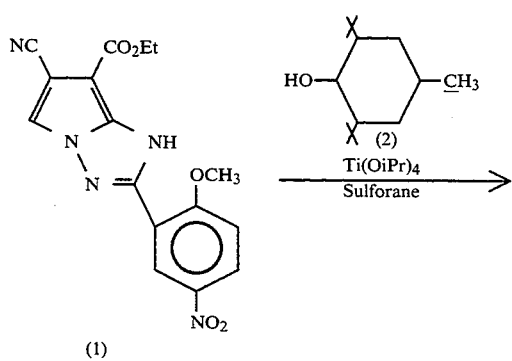

Precisely, 3.00 g of compound (1), 7.78 g of compound (2) and 1.00 g of Ti(OiPr)$_4$ were dissolved in 4 ml of sulforane and heated at 170° C. for 2 days. This was cooled, stirred with ethyl acetate and water and filtered through silica gel. The organic layer was separated and dried with MgSO$_4$. This was concentrated, and 5 g of the thus-concentrated black oil was purified by silica gel column chromatography (using hexane/ethyl acetate=2/1) to obtain 0.91 g of an amorphous product of compound (3). The yield of the product was 20%.

Compound (2) was produced according to the method described in J.A.C.S., 79 (1957) 5019, ibid., 69 (1947) 2414.

1.02 g of reduced iron, 0.12 g of NH4Cl, 22.5 ml of isopropyl alcohol (IPA) and 2.5 ml of water were stirred on a steam bath, and compound (3) that had been produced previously was added thereto along with 10 ml of IPA and then stirred vigorously. After 35 minutes, the finish of the reaction was confirmed by thin layer chromatography, and the reaction mixture was filtered through silica gel while hot. This was concentrated to obtain 0.87 g of pale brown crystals. 20 ml of DMF and 0.92 g of compound (4) were added thereto and stirred for a while at room temperature, and 0.16 ml of pyridine were added thereto slowly. Then, this was allowed to stand at room temperature overnight. This was extracted with ethyl acetate and dried with MgSO4. The concentrated residue was purified by column chromatography to obtain 0.45 g of an amorphous product of compound (5).

The thus-obtained compound (5) was easily chlorinated with one equivalent amount of $SO_2Cl_2$ in $CH_2Cl_2$ at room temperature. After this was purified through a column, 0.42 g of compound (7) was obtained.

PRODUCTION EXAMPLE 2

Production of Compound (53)

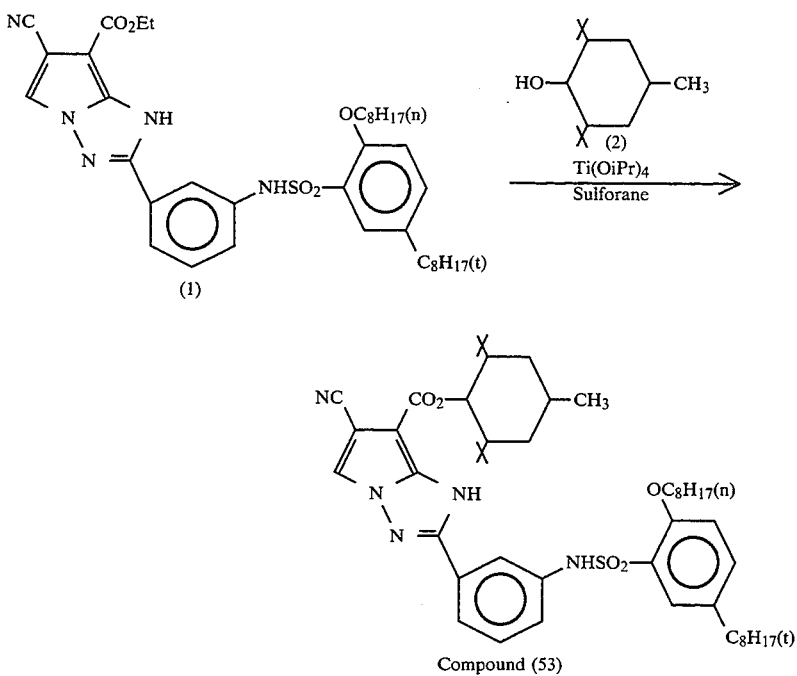

Compound (53)

Precisely, 1.54 g of compound (1), 2.58 g of compound (2) and 0.32 g of Ti(OiPr)4 were dissolved in 2 ml of sulforane and stirred under heat at 155° C. for 6 hours. This was cooled, stirred along with ethyl acetate and water and filtered through Celite. The organic layer was separated, dried with MgSO4 and then concentrated to obtain 3.40 g of a brown oil. This was purified by silica gel column chromatography .(using hexane/ethyl acetate=20/1) to obtain 1.25 g of crystals of compound (53). The yield of the product was 64%.

The other compounds of the present invention may be produced in accordance with the same methods as mentioned above.

The photographic material of the present invention may be one which has at least one layer containing the cyan coupler(s) of the present invention on a support. The layer of containing the cyan coupler(s) of the present invention may be a hydrophilic colloid layer on a support. An ordinary photographic material has at least one blue-sensitive silver halide emulsion layer, at least one green-sensitive silver halide emulsion layer and at least one red-sensitive silver halide emulsion layer on a support in this order, and the order of the constitutive layers on the support may be different from the said one. The material may contain an infrared-sensitive silver halide emulsion layer in place of at least one of the above-mentioned light-sensitive emulsion layers. These light-sensitive emulsion layers each may comprise a silver halide emulsion having a sensitivity to the respective wavelength range and a color coupler of forming a dye having a complementary color to the light to which the emulsion is sensitive, whereby color reproduction by subtractive color photography may be effected. The relationship between the light-sensitive emulsion layer and the color hue of the dye to be formed from the color coupler in the layer is not limited to the above-mentioned constitution but may be of any others.

Where the cyan couplers of the present invention are applied to photographic materials, they are preferably incorporated into the red-sensitive silver halide emulsion layer of the material.

The content of the cyan coupler(s) of the present invention in the photographic material may be from $1 \times 10^{-3}$ mol to 1 mol, preferably from $2 \times 10^{-3}$ mol to $3 \times 10^{-1}$ mol, per mol of the silver halide in the layer containing the cyan coupler(s).

The cyan couplers of the present invention can be introduced into the photographic material by various known methods. Preferred is an oil-in-water dispersion method in which the coupler is dissolved in a high boiling point organic solvent (if desired, along with a low boiling point organic solvent) and the resulting solution is dispersed in an aqueous gelatin solution by emulsification and added to a silver halide emulsion.

Examples of high boiling point solvents to be used in an oil-in-water dispersion method which may be employed in the present invention are described in U.S. Pat. No. 2,322,027. As one polymer dispersion method, known is a latex dispersion method which may also be employed in the present invention. The process of such a latex dispersion method, the effect of the same and specific examples of latexes for impregnation to be used in the method are described in U.S. Pat. No. 4,199,363, German Patent OLS Nos. 2,541,274 and 2,541,230, JP-B-53-41091 and European Patent Laid-Open No. 029104. A dispersion method of using organic solvent-soluble polymers may also be employed in the present invention, which is described in PCT Laid-Open WO88/00723.

As examples of high boiling point organic solvents usable in the above-mentioned oil-in-water method, there are mentioned phthalates (e.g., dibutyl phthalate, dioctyl phthalate, dicyclohexyl phthalate, di-2-ethylhexyl phthalate, decyl phthalate, bis(2,4-di-t-amylphenyl) isophthalate, bis(1,1-diethylpropyl) phthalate), phosphates or phosphonates (e.g., diphenyl phosphate, triphenyl phosphate, tricresyl phosphate, 2-ethylhexyldiphenyl phosphate, dioctylbutyl phosphate, tricyclohexyl phosphate, tri-2-ethylhexyl phosphate, tridodecyl phosphate, di-2-ethylhexylphenyl phosphonate), benzoates (e.g., 2-ethylhexyl benzoate, 2,4-dichlorobenzoate, dodecyl benzoate, 2-ethylhexyl-p-hydroxybenzoate), amides (e.g., N,N-diethyidodecanamide, N,N-diethyllaurylamide), alcohols or phenols (e.g., isostearyl alcohol, 2,4-di-tert-amylphenol), aliphatic esters (e.g., dibutoxyethyl succinate, di-2-ethylhexyl succinate, 2-hexyldecyl tetradecanoate, tributyl citrate, diethyl azelate, isostearyl lactate, trioctyl citrate), aniline derivatives (e.g., N,N-dibutyl-2-butoxy-5-tert-octylaniline), chlorinated paraffins (e.g., paraffins having chlorine content of from 10% to 80%), trimesates (e.g., tributyl trimesate), dodecylbenzene, diisopropylnaphthalene, phenols (e.g., 2,4-di-tert-amylphenol, 4-dodecyloxyphenol, 4-dodecyloxycarbonylphenol 4-(4-dodecyloxyphenylsulfonyl)phenol), carboxylic acids (e.g., 2-(2,4-di-tert-amylphenoxybutyric acid, 2-ethoxyoctanedecanoic acid), and alkylphosphoric acids (e.g., di-(2-ethylhexyl)phosphoric acid, diphenylphosphoric acid). As auxiliary solvents usable along with the high boiling point organic solvents, there are mentioned, for example, organic solvents having a boiling point of approximately from 30° C. to 160° C., such as ethyl acetate, butyl acetate, ethyl propionate, methyl ethyl ketone, cyclohexanone, 2-ethoxyethyl acetate, and dimethylformamide.

The proportion of the high boiling point organic solvent to be used in the case may be from. 0 to 10.0 times, preferably from 0 to 5.0 times, more preferably from 0.5 to 4.5 times, to the coupler.

As silver halide .emulsions and other elements (e.g., additives, etc.) of constituting the photographic material of the present invention, photographic layers of constituting the material (e.g., arrangement of layers), and methods of processing the material and additives usable in the processing methods, those described in the following patent publications, especially in European Patent 0,355,660A2, are preferably employed.

| Photographic Elements | JP-A 62-215272 | JP-A 2-33144 | EP 0,355,660A2 |
| --- | --- | --- | --- |
| Silver Halide Emulsions | From page 10, right upper column, line 6 to page 12, left lower column, line 5; and from page 12, right lower column, line 4 to page 13, left upper column, line 17 | From page 28, right upper column, line 16 to page 29, right lower column, line 11; and page 30, lines 2 to 5 | From page 45, line 53 to page 47, line 3; and page 47, lines 20 to 22 |
| Silver Halide Solvents | Page 12, left lower column, lines 6 to 14; and from page 13, left upper column, line 3 from below to page 18, left lower column, last line | — | — |
| Chemical Sensitizers | Page 12, from left lower column, line 3 from below to right lower column, line 5 from below; and from page 18, right lower column, line 1 to page 22, right upper column, line 9 from below | Page 29, right lower column, line 12 to last line | Page 47, lines 4 to 9 |
| Color Sensitizers (Color Sensitizing Methods) | From page 22, right upper column, line 8 from below to page 38, last line | Page 30, left upper column, lines 1 to 13 | Page 47, lines 10 to 15 |
| Emulsion Stabilizers | From page 39, left upper column, line 1 to page 72, right upper column, last line | Page 30, from left upper column, line 14 to right upper column, line 1 | Page 47, lines 16 to 19 |
| Development Promoters | From page 72, left lower column, line 1 to page 91, right upper column, line 3 | — | — |
| Color Couplers (Cyan, Magenta and Yellow Couplers) | From page 91, right upper column, line 4 to page 121, left upper column, line 6 | From page 3, right upper column, line 14 to page 18, left upper column, last line; and from page 30, right upper column, line 6 to page 35, right lower column, line 11 | Page 4, lines 15 to 27; from page 5, line 30 to page 8, last line; page 45, lines 29 to 31; and from page 47, line 23 to page 63, line 50 |
| Coloring Enhancers | From page 121, left upper column, line 7 to page 125, right upper column, line 1 | — | — |
| Ultraviolet Absorbents | From page 125, right upper column, line 2 to page 127, left lower column, last line | From page 37, right lower column, line 14 to page 38, left upper column, line 11 | Page 65, lines 22 to 31 |
| Anti-fading Agents (Color Image Stabilizers) | From page 127, right lower column, line 1 to page 137, left lower column, line 8 | From page 36, right upper column, line 12 to page 37, left upper column, line 19 | From page 4, line 30 to page 5, line 23; from page 29, line l to page 45, line 25; page 45, |

-continued

| Photographic Elements | JP-A 62-215272 | JP-A 2-33144 | EP 0,355,660A2 |
|---|---|---|---|
| | | | lines 33 to 40; and page 65, lines 2 to 21 |
| High Boiling Point and/or Low Boiling Point Organic Solvents | From page 137, left lower column, line 9 to page 144, right upper column, last line | From page 35, right lower column, line 14 to page 36, left upper column, line 4 from below | Page 64, lines 1 to 51 |
| Dispersing Methods of Photographic Additives | From page 144, left lower column, line 1 to page 146, right upper column, line 7 | From page 27, right lower column, line 10 to page 28, left upper column, last line; and from page 35, right lower column, line 12, to page 36, right upper column, line 7 | From page 63, line 51 to page 64, line 56 |
| Hardening Agents | From page 146, right upper column, line 8 to page 155, left lower column, line 4 | — | — |
| Developing Agent Precursors | Page 155, from left lower column, line 5 to right lower column, line 2 | — | — |
| Development Inhibitor Releasing Compounds | Page 155, right lower column, lines 3 to 9 | — | — |
| Supports | From page 155, right lower column, line 19 to page 156, left upper column, line 14 | From page 38, right upper column, line 18 to page 39, left upper column, line 3 | From page 66, line 29 to page 67, line 13 |
| Constitution of Photographic Layers | Page 156, from left upper column, line 15 to right lower column, line 14 | Page 28, right upper column, lines 1 to 15 | Page 45, lines 41 to 52 |
| Dyes | From page 156, right lower column, line 15 to page 184, right lower column, last line | Page 38, from left upper column, line 12 to right upper column, line 7 | Page 66, lines 18 to 22 |
| Color Mixing Preventing Agents | From page 185, left upper column, line 1 to page 188, right lower column, line 3 | Page 36, right lower column, lines 8 to 11 | From page 64, line 57 to page 65, line 1 |
| Gradation Adjusting Agents | Page 188, right lower column, lines 4 to 8 | — | — |
| Stain Inhibitors | From page 188, right lower column, line 9 to page 193, right lower column, line 10 | Page 37, from left upper column, last line to right lower column, line 13 | From page 65, line 32 to page 66, line 17 |
| Surfactants | From page 201, left lower column, line 1 to page 210, right upper column, last one | From page 18, right upper column, line 1 to page 24, right lower column, last line; and page 27, from left lower column, line 10 from below to right lower column, line 9 | — |
| Fluorine-containing Compounds (as antistatic agents, coating aids, lubricants, and anti-blocking agents) | From page 210, left lower column, line 1 to page 222, left lower column, line 5 | From page 25, left upper column, line 1 to page 27, right lower column, line 9 | — |
| Binders (hydrophilic colloids) | From page 222, left lower column, line 6 to page 225, left upper column, last line | Page 38, right upper column, lines 8 to 18 | Page 66, lines 23 to 28 |
| Tackifiers | From page 225, right upper column, line 1 to page 227, right upper column, line 2 | — | — |
| Antistatic Agents | From page 227, right upper column, line 3 to page 230, left upper column, line 1 | — | — |
| Polymer Latexes | From page 230, left upper column, line 2 to page 239, last line | — | — |
| Mat Agents, | Page 240, from left upper column, line 1 to right upper column, last line | — | — |
| Photographic Processing Methods (Processing steps and additives) | From page 3, right upper column, line 7 to page 10, right upper column, line 5 | From page 39, left upper column, line 4 to page 42, left upper column, last line | From page 67, line 14 to page 69, line 28 |

Remarks: The cited specification of JP-A-62-215272 is one as amended by the letter of amendment filed on March 16, 1987.

In addition, the silver halide color photographic materials and the methods for processing them described in JP-A-5-34889, JP-A-4-359249, JP-A-4-313753, JP-A-4-270344, JP-A-5-66527, JP-A-4-34548, JP-A-4-145433, JP-A-2-854, JP-A-1-158431, JP-A-2-90145, JP-A-3-194539, JP-A-2-93641, European Patent 0520457A2 are also preferably referred to.

Silver halides to be used for constituting the photographic material of the present invention include silver chloride, silver bromide, silver chlorobromide, silver iodochlorobromide and silver iodobromide. For the purpose of rapidly processing the photographic material, preferred is a silver chlorobromide emulsion having a silver chloride content of 90 mol % or more, preferably 95 mol % or more, especially preferably 98 mol % or more, or a pure silver chloride -emulsion, which does not substantially contain silver iodide.

For the purpose of improving the sharpness of the image to be formed on the photographic material of the present invention, it is preferred to incorporate a dye capable of being decolored by photographic processing, as described in European Patent 0,337,490A2 (especially oxonole dyes), into the hydrophilic colloid layer of the material in such an amount that the optical reflection density of the material at 680 nm may be 0.70 or more, or to incorporate a titanium oxide as surface-treated with a di-hydric to tetra-hydric alcohol (e.g., trimethylolethane) into the water-proof resin layer of the support of the material in an amount of 12% by weight or more, more preferably 14% by weight or more.

The photographic material of the present invention preferably contains a color image preservability improving compound, for example, one as described in European Patent 0,277,589A2, along with couplers. Incorporation of such a color image preservability improving compound into the material along with a pyrazoloazole magenta coupler is preferred.

Specifically, single or combined incorporation of a compound (F) described in European Patent 0,277,589A2, which may bind with the aromatic amine developing agent as remained in the photographic material after color development thereof by chemical bond between them to form a chemically inactive and substantially colorless compound and/or a compound (G) described in European Patent 0,277,589A2, which may bind with the oxidation product of an aromatic amine developing agent as remained in the photographic material after color development thereof by chemical bond between them to form a chemically inactive and substantially colorless compound into the photographic material of the present invention is preferred for the purpose of preventing formation of color dyes by reaction of the color developing agent or the oxidation product thereof as remained in the photographic material and couplers in the material during storage of the processed material to cause formation of stains in the processed material during storage thereof and also preventing any other harmful side effect of the remained agent and oxidation product of thereof.

The photographic material of the present invention also preferably contain a microbicide, such as one as described in JP-A-63-271247, for the purpose of preventing propagation of various fungi and bacteria in the hydrophilic colloid layer of the processed material which would deteriorate the image formed on the material.

As a support to be in the photographic material of the present invention, a white polyester support or a support having a white pigment-containing layer on the side to face with silver halide emulsion layers as coated thereover may be employed for displays. In order to improve the sharpness of the image to be formed, it is preferred to provide an anti-halation layer on the support on either of the side to face with silver halide emulsion layers as coated thereover or the opposite back side thereto. In particular, it is preferred to define the transmission density of the support-to fall within the range of from 0.35 to 0.8, in order that the display with the photographic material of the present invention be may seen either with a reflecting light or a transmitting light.

The photographic material of the present invention may be exposed either with visible rays or with infrared rays. For exposure of the material, either low intensity exposure or high intensity short-time exposure may be employed. In particular, in the latter case, a laser scanning exposure system is preferred where the exposure time is shorter than $10^{-4}$ second per pixel.

In exposure of the photographic material of the present invention, a band stop filer described in U.S. Pat. No. 4,880,726 is preferably used. Using it, rays of causing light stain may be removed so that the color reproducibility of the exposed material is improved noticeably.

Next, the present invention will be explained in more detail by means of the following examples, which, however, are not intended to restrict -the scope of the present invention.

EXAMPLE 1

Plural photographic constitutive layers each having the composition mentioned below were coated ever a paper support, of which the both surfaces had been laminated with polyethylene, to form a multi-layer color photographic paper (sample No. 109). Coating liquids were prepared in the manner mentioned below.

Preparation of Coating Liquid for Fifth Layer 20.0 g of cyan coupler (Compound (1) mentioned hereinabove), 30.0 g of color image stabilizer (Cpd-1), 5.0 g of color image stabilizer (Cpd-2), 8.0 g of color image stabilizer (Cpd-5), 1.0 g of color image stabilizer (Cpd-6), 10.0 g of color image stabilizer (Cpd-8), 1.0 g of color image stabilizer (Cpd-9), 15.0 g of color image stabilizer (Cpd-10), 1.0 g of color image stabilizer (Cpd-11), 35.0 g of solvent (Solv-2), 35.0 g of solvent (Solv-9) and 5.0 g of sodium dodecylbenzenesulfonate were dissolved in 80 ml of ethyl acetate, and the resulting solution was emulsified and dispersed in an aqueous 20% gelatin solution, using a high-speed stirring emulsifier.

On the other hand, silver chlorobromide emulsion C (5/5 (by mol of silver) mixture of large-size emulsion $R_1$ of cubic grains with a mean grain size of 0.60 μm and small-size emulsion $R_2$ of cubic grains with a mean grain size of 0.48 μm; the fluctuation coefficient of the grain size distribution of the two emulsions was 0.06 and 0.08, respectively; the silver halide grains in the both emulsions had 0.5 mol % of silver bromide locally on a part of the surface of each grain while having silver chloride on the remaining part of the surface thereof) was prepared. The emulsion contained the following red-sensitizing dye E in an amount of $1.0 \times 10^{-4}$ mol per mol of silver in the large-size emulsion and $1.2 \times 10^{-4}$ mol per mol of silver in the small-size emulsion. Chemical ripening of the emulsion was effected by sulfur sensitization and gold sensitization. The emulsified dispersion as previously prepared and the silver chlorobromide emulsion were blended to give a coating liquid for the fifth layer having the composition mentioned below.

The other coating liquids for the first to seventh layers were also prepared in the same manner as in preparation of the coating liquid for the fifth layer. As a gelatin hardening agent for each layer, added thereto was 1-hydroxy-3,5-dichloro-s-triazine sodium salt.

The respective layers contained 25.0 mg/m², as a whole, of Cpd-14 and 50 mg/m², as a whole, of Cpd-15.

Silver chlorobromide emulsions for the other light-sensitive emulsion layers Were prepared in the same manner as in preparation of the above-mentioned silver chlorobromide emulsion C, except that the size and the halogen composition of the silver halide grains were varied and the color-sensitizing dyes mentioned below were added.

Blue-sensitive Emulsion Layer

Sensitizing Dye A

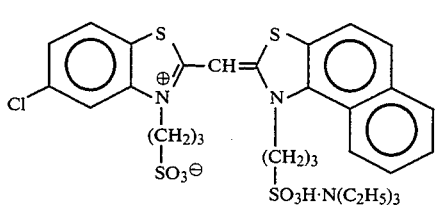

($2.0\times10^{-4}$ mol per mol of silver halide to large-size emulsion; and $2.5\times10^{-4}$ mol per mol of silver halide to small-size emulsion)

Sensitizing Dye B

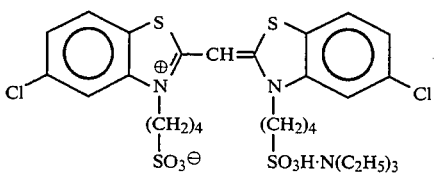

($2.0\times10^{-4}$ mol per mol of silver halide to large-size emulsion; and $2.5\times10^{-4}$ mol per mol of silver halide to small-size emulsion)

Green-sensitive Emulsion Layer

Sensitizing Dye C

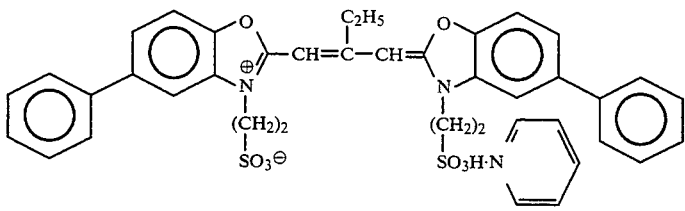

($4.0\times10^{-4}$ mol per mol of silver halide to large-size emulsion; and $5.6\times10^{-4}$ mol per mol of silver halide to small-size emulsion)

Sensitizing Dye D

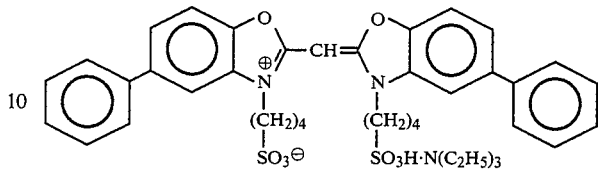

($7.0\times10^{-5}$ mol per mol of silver halide to large-size emulsion; and $1.0\times10^{-4}$ mol per mol of silver halide to small-size emulsion)

Red-sensitive Emulsion Layer

Sensitizing Dye E

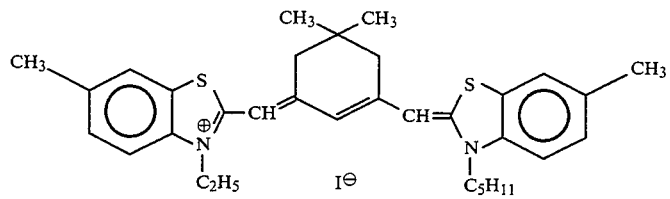

($1.0\times10^{-4}$ mol per mol of silver halide to large-size emulsion; and $1.2\times10^{-4}$ mol per mol of silver halide to small-size emulsion) In addition, the following compound was added in an amount of $2.6\times10^{-3}$ mol per mol of silver halide.

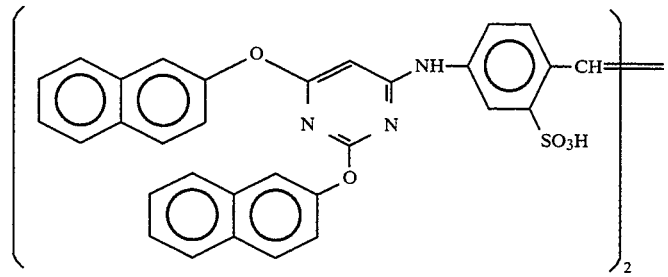

To the blue-sensitive emulsion layer, the green-sensitive emulsion layer and the red-sensitive emulsion layer was added 1-(5-methylureidophenyl)-5-mercaptotetrazole each in an amount of $2.5\times10^{-3}$ mol, $4.0\times10^{-3}$ mol and $2.5\times10^{-4}$ mol, per mol of silver halide, respectively.

To the blue-sensitive emulsion layer and the green-sensitive emulsion Layer was added 4-hydroxy-6-methyl-1,3,3a,7-tetrazaindene each in an amount of $1\times10^{-4}$ mol and $2 \times 10^{-4}$ mol, per mol of silver halide, respectively.

For anti-irradiation, the following dyes were added to the respective emulsion layers, the coated amount being parenthesized.

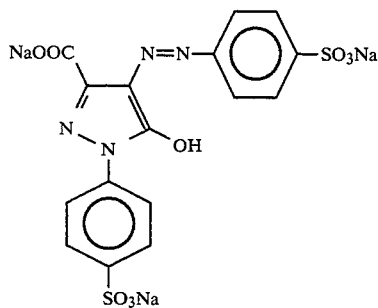

(10 mg/m$^2$)

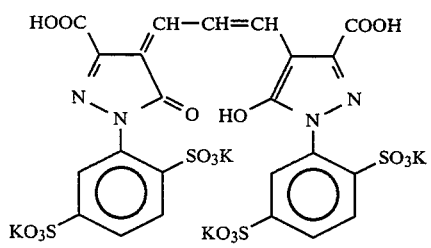

(10 mg/m$^2$)

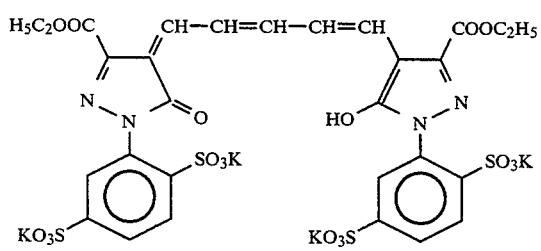

(40 mg/m$^2$)

and

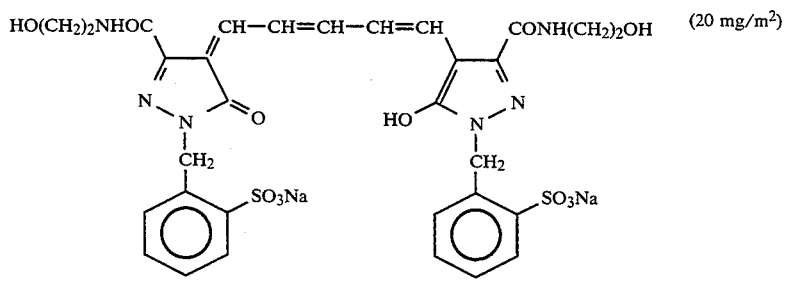

(20 mg/m$^2$)

Layer Constitution

Compositions of the layers of constituting sample No. 109 are mentioned below, in which the numerical value indicates the amount coated (g/m$^2$) and the amount of the silver halide coated is represented as silver therein.

Support:

Polyethylene-laminated Paper (This contained white pigment (TiO$_2$, 14% by weight) and bluish dye (ultramarine) in polyethylene below the first layer. The centerline surface roughness of the surface of the support to be coated with the first layer was 0.13 μm.)

First Layer: Blue-sensitive Emulsion Layer

| | |
|---|---|
| Silver Chlorobromide Emulsion A (3/7 (by mol of silver) mixture of large-size emulsion of cubic grains with a mean grain size of 0.88 μm and small-size emulsion of cubic grains with a mean grain size of 0.70 μm; the fluctuation coefficient of the grain size distribution of the two emulsions was 0.08 and 0.10, respectively; the silver halide grains in the both emulsions had 0.3 mol % of silver bromide locally on a part of the surface of each grain while having 0.1 mg, as a whole, of potassium hexachloroiridate(IV) and 1.0 mg, as a whole, of potassium ferrocyanide in the inside and the local silver bromide phase in each grain) | 0.24 |
| Gelatin | 1.36 |
| Yellow Coupler (ExY) | 0.65 |
| Color Image Stabilizer (Cpd-1) | 0.16 |
| Color Image Stabilizer (Cpd-2) | 0.08 |
| Color Image Stabilizer (Cpd-3) | 0.08 |
| Solvent (Solv-1) | 0.13 |
| Solvent (Solv-5) | 0.13 |

Second Layer: Color Mixing Preventing Layer

| | |
|---|---|
| Gelatin | 0.80 |
| Color Mixing Preventing Agent (Cpd-4) | 0.11 |
| Solvent (Solv-7) | 0.03 |
| Solvent (Solv-2) | 0.25 |
| Solvent (Solv-3) | 0.25 |

Third Layer: Green-sensitive Emulsion Layer

| | |
|---|---|
| Silver Chlorobromide Emulsion B (⅓ mixture (by mol of Ag) of large-size emulsion of cubic grains with a mean grain size of 0.55 μm and small-size emulsion of cubic grains with a mean grain size of 0.39 μm; the two emulsions each had a fluctuation coefficient of the grain size distribution of 0.10 and 0.08, respectively; they contained 0.8 mol % of silver bromide locally on a part of the surface of each grain, while having 0.2 mg, as a whole, of potassium hexachloroiridate(IV) and 1.0 mg, as a whole, of potassium ferrocyanide in the inside and the local silver bromide phase in each grain; they had been subjected to optimum chemical sensitization with a sulfur sensitizer and a gold sensitizer in the presence of a decomposate of nucleic acid) | 0.13 |
| Gelatin | 1.40 |
| Magenta Coupler (ExM) | 0.18 |
| Color Image Stabilizer (Cpd-5) | 0.15 |
| Color Image Stabilizer (Cpd-2) | 0.03 |
| Color Image Stabilizer (Cpd-6) | 0.01 |
| Color Image Stabilizer (Cpd-7) | 0.01 |
| Color Image Stabilizer (Cpd-8) | 0.08 |
| Solvent (Solv-3) | 0.20 |
| Solvent (Solv-4) | 0.35 |
| Solvent (Solv-8) | 0.35 |

Fourth Layer: Color Mixing Preventing Layer

| | |
|---|---|
| Gelatin | 0.65 |
| Color Mixing Preventing Agent (Cpd-4) | 0.08 |
| Solvent (Solv-7) | 0.02 |
| Solvent (Solv-2) | 0.18 |
| Solvent (Solv-3) | 0.18 |

Fifth Layer: Red-sensitive Emulsion Layer

| | |
|---|---|
| Above-mentioned Silver Chlorobromide Emulsion C | 0.13 |
| Gelatin | 1.61 |
| Cyan Coupler (compound (1) mentioned above) | 0.20 |
| Color Image Stabilizer (Cpd-1) | 0.30 |
| Color Image Stabilizer (Cpd-2) | 0.05 |
| Color Image Stabilizer (Cpd-5) | 0.08 |
| Color Image Stabilizer (Cpd-6) | 0.01 |
| Color Image Stabilizer (Cpd-8) | 0.10 |
| Color Image Stabilizer (Cpd-9) | 0.01 |
| Color Image Stabilizer (Cpd-10) | 0.15 |
| Color Image Stabilizer (Cpd-11) | 0.01 |
| Solvent (Solv-2) | 0.35 |
| Solvent (Solv-9) | 0.35 |

Sixth Layer: Ultraviolet Absorbing Layer

| | |
|---|---|
| Gelatin | 0.50 |
| Ultraviolet Absorbent (UV-1) | 0.38 |
| Color Image Stabilizer (Cpd-5) | 0.02 |
| Color Image Stabilizer (Cpd-12) | 0.15 |

Seventh Layer: Protective Layer

| | |
|---|---|
| Gelatin | 1.00 |
| Acryl-modified Copolymer of Polyvinyl Alcohol (modification degree 17%) | 0.05 |
| Liquid Paraffin | 0.02 |
| Color Image Stabilizer (Cpd-13) | 0.01 |

The compounds used above are mentioned below.

(ExY) Yellow Coupler:

25/25/25/25 (by mol) mixture of the following ①, ②, ③, ④:

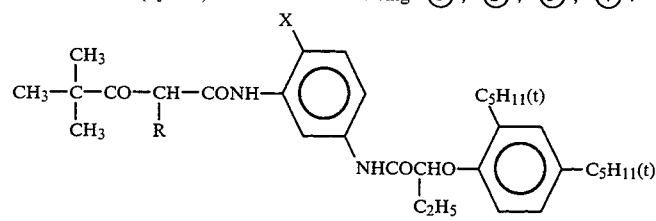

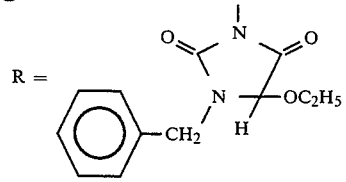

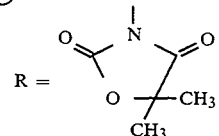

③
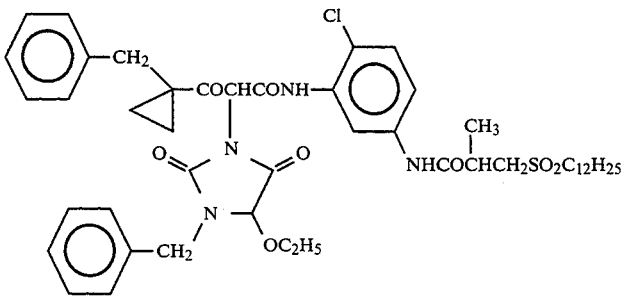
④
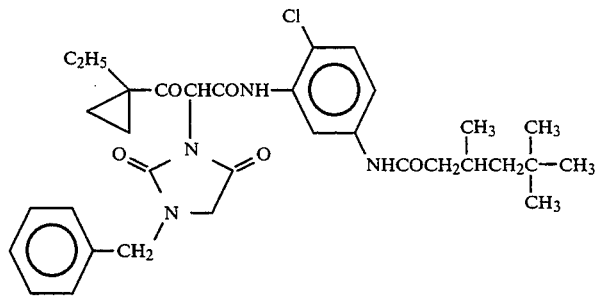
(ExM) Magenta Coupler:
1/1 (by mol) mixture of the following ①, ②:
①
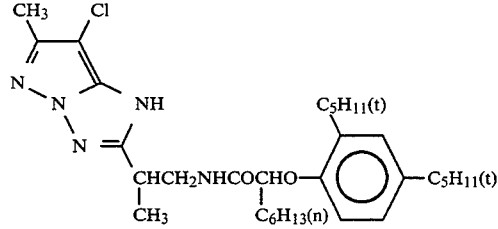
②
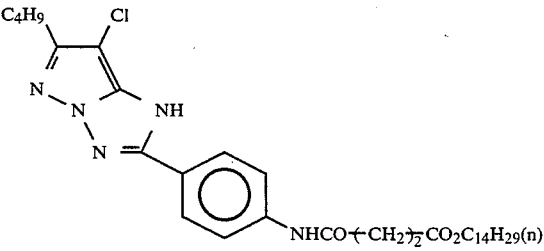
(Cpd-1) Color Image Stabilizer:
(mean molecular weight: 60,000)
(Cpd-2) Color Image Stabilizer:
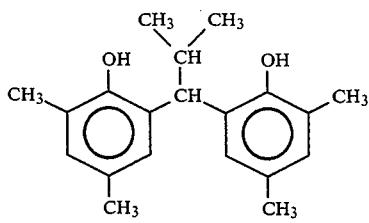
(Cpd-3) Color Image Stabilizer:
(Cpd-4) Color Mixing Preventing Agent:

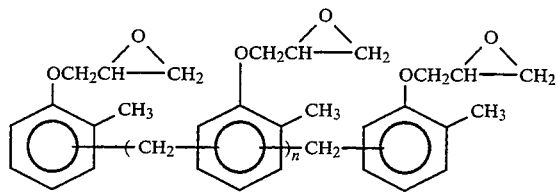

n = 7 to 8 (mean value)

1/1/1 (by mol) mixture of the following ①, ②, ③:

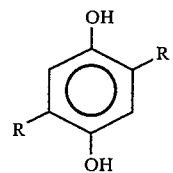

(Cpd-5) Color Image Stabilizer:

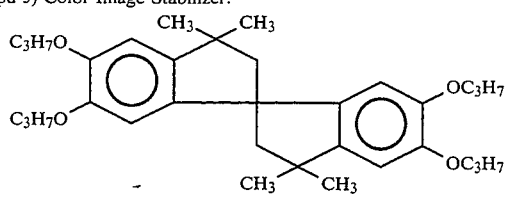

(Cpd-6) Color Image Stabilizer:

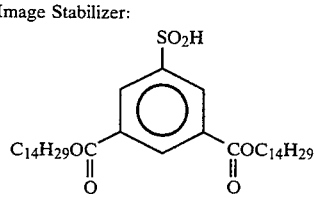

(Cpd-7) Color Image Stabilizer:

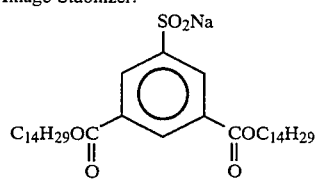

(Cpd-8) Color Image Stabilizer:

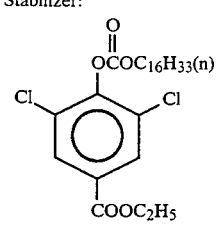

(Cpd-9) Color Image Stabilizer:

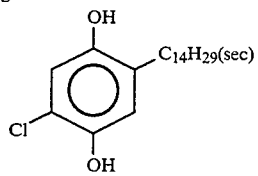

(Cpd-10) Color Image Stabilizer:

1/1/2/2 (by weight) mixture of the following (i), (ii), (iii), (iv):

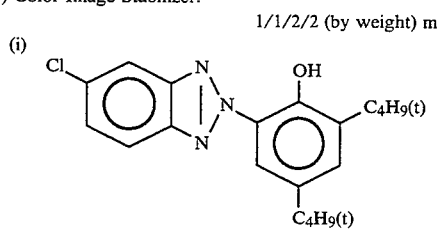

(Cpd-11) Color Image Stabilizer:

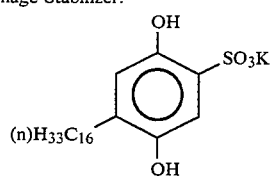

(Cpd-12) Color Image Stabilizer:

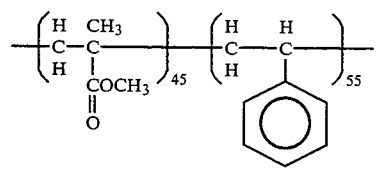

(mean molecular weight: about 60,000)

(Cpd-13) Color Image Stabilizer:

(Cpd-14) Antiseptic:

$$C_{13}H_{27}CONH(CH_2)_3 \overset{CH_3}{\underset{CH_3}{\overset{|}{\underset{|}{\oplus}}}} NCH_2COO^{\ominus}$$

[Structure: benzisothiazolinone — benzene ring fused with S-NH-C(=O) ring]

(Cpd-15) Antiseptic:

HO—⟨C₆H₄⟩—COOC₄H₉

(UV-1) Ultraviolet Absorbent:

1/5/10/5/5 (by weight) mixture of the following (i), (ii), (iii), (iv), (v):

(i) 5-Chloro-benzotriazole-2-yl linked to 2-hydroxy-3,5-di-t-butylphenyl (C₄H₉(t), C₄H₉(t), OH)

(ii) Benzotriazole-2-yl linked to 2-hydroxy-5-dodecylphenyl (OH, C₁₂H₂₅)

(iii) 5-Chloro-benzotriazole-2-yl linked to 2-hydroxy-3-t-butyl-5-(CH₂)₂COOC₈H₁₇ phenyl (OH, C₄H₉(t), (CH₂)₂COOC₈H₁₇)

(iv) Benzotriazole-2-yl linked to 2-hydroxy-3,5-di-t-pentylphenyl (OH, C₅H₁₁(t), C₅H₁₁(t))

(v) Benzotriazole-2-yl linked to 2-hydroxy-5-t-octylphenyl (OH, C₈H₁₇(t))

(Solv-1) Solvent:

$$C_8H_{17}\underset{\underset{O}{\diagdown\diagup}}{CHCH}(CH_2)_7COOC_8H_{17}$$

(Solv-2) Solvent:

⟨C₆H₄⟩ with COOC₄H₉, COOC₄H₉ (ortho)

(Solv-3) Solvent:

$$O=P{\left[O{-}⟨C_6H_4⟩{-}CH_3\right]}_3$$

(Solv-4) Solvent:

$$\begin{array}{c} COOC_4H_9 \\ | \\ (CH_2)_8 \\ | \\ COOC_4H_9 \end{array}$$

(Solv-5) Solvent:

$$O=P{\left(OCH_2\underset{\underset{C_2H_5}{|}}{CH}C_4H_9(n)\right)}_3$$

(Solv-6) Solvent:

⟨C₆H₄⟩ with COO—⟨C₆H₁₁⟩, COO—⟨C₆H₁₁⟩ (ortho) (dicyclohexyl phthalate)

(Solv-7) Solvent:

HO—⟨C₆H₄⟩—COOC₁₆H₃₃(n)

(Solv-8) Solvent:

$$O=P{(O{-}C_6H_{13})}_3$$

(Solv-9) Solvent:

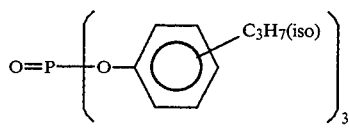

Other samples (Nos. 101 to 108 and 110 to 115) were prepared in the same manner as in preparation of sample No. 108, except that the coupler in the fifth layer was varied to that indicated in Table A below.

The samples were exposed and then processed in the manner mentioned below.

Exposure

Using a sensitometer (FWH Model, manufactured by Fuji Photo Film Co.; with a color temperature of the light source of being 3200° K.), sample No. 107 was exposed to such a degree that about 30% of the coated silver is developed to give gray color.

The exposed sample was processed with a paper processing machine in accordance with the process mentioned below, until the total amount of the replenisher to the color developer tank became two times the tank capacity.

| Processing Step | Process: Temperature | Time | Amount of Replenisher (*) | Tank Capacity |
|---|---|---|---|---|
| Color Development | 38.5° C. | 45 sec | 73 ml | 10 liters |
| Blix | 35° C. | 45 sec | 60 ml | 10 liters |
| Rinsing ① | 35° C. | 20 sec | — | 5 liters |
| Rinsing ② | 35° C. | 20 sec | — | 5 liters |
| Rinsing ③ | 30 to 35° C. | 20 sec | 360 ml | 5 liters |
| Drying | 70 to 80° C. | 60 sec | | |

(*) per m² of sample being processed.
(Rinsing was effected by three-tank countercurrent cascade system from ③ to ①.)

Compositions of the processing solutions used above are mentioned below.

| Color Developer | Tank Solution | Replenisher |
|---|---|---|
| Water | 700 ml | 700 ml |
| Sodium Triisopropylnaphthalene(β)sulfonate | 0.1 g | 0.1 g |
| Ethylenediaminetetraacetic Acid | 3.0 g | 3.0 g |
| Disodium 1,2-Dihydroxybenzene-4,6-disulfonate | 0.5 g | 0.5 g |
| Triethanolamine | 12.0 g | 12.0 g |
| Potassium Chloride | 6.5 g | — |
| Potassium Bromide | 0.03 g | — |
| Potassium Carbonate | 27.0 g | 27.0 g |
| Brightening Agent (WHITEX 4B, made by Sumitomo Chemical Co.) | 1.0 g | 3.0 g |
| Sodium Sulfite | 0.1 g | 0.1 g |
| Disodium N,N-bis(sulfonatoethyl)hydroxylamine | 10.0 g | 13.0 g |
| N-ethyl-N-(β-methanesulfonamidoethyl)-3-methyl-4-aminoaniline Sulfate | 5.0 g | 11.5 g |
| Water to make | 1000 ml | 1000 ml |
| pH (25° C.) | 10.00 | 11.00 |

| Blix Solution | Tank Solution | Replenisher |
|---|---|---|
| Water | 600 ml | 600 ml |
| Ammonium Thiosulfate (700 g/liter) | 100 ml | 250 ml |
| Ammonium Sulfite | 20 g | 100 g |
| Ammonium Ethylenediaminetetraacetato/Iron(III) | 55 g | 135 g |
| Disodium Ethylenediaminetetraacetate | 5 g | 12.5 g |
| Ammonium Bromide | 40 g | 75 g |
| Nitric Acid (67%) | 30 g | 65 g |
| Water to make | 1000 ml | 1000 ml |
| pH (25° C.) | 5.80 | 5.60 |

Rinsing Solution

Ion-exchanged Water (having calcium and magnesium content of 3 ppm or less each).

Next, using the above-mentioned sensitometer, all the samples were stepwise exposed through a color-separation filter. The exposed samples were then processed, using the running solutions that had been prepared by the above-mentioned continuous-processing. The thus-processed samples were evaluated with respect to their photographic properties by the methods mentioned below.

Evaluation 1: Color Hue (Y/C)

The yellow density at the point giving a cyan density of 1.0 in the cyan-colored layer was measured, using a densitometer, X-Rite 310 Model (made by X-Rite Co.). The smaller the yellow density, the smaller the side-absorption and therefore the better the color hue.

Evaluation 2: Variation in Color Density Due to Fluctuation of Composition of Blix Solution Used Using the running solutions, the exposed samples were processed by two methods. In one method, used was a fresh blix solution; while in the other method, used was a blix solution containing twice the amount of ammonium thiosulfite and twice the amount of ammonium sulfite. The decrease in the maximum cyan color density due to the change of the blix solutions used was represented by percentage.

Evaluation 3: Color Image Fastness

The processed samples were stored at 100° C. for 2 days and at 80° C. and 70% RH for 6 days. The decrease in the density of each sample before and after the storage was measured at the point having an initial density of 0.6. The decrease in the density was represented by percentage.

Evaluation 4: Color Fog

The cyan reflection density in the unexposed area in each sample was measured, using a densitometer X-Rite 310 Model.

The data of the thus-tested sample Nos..101 to 115 are shown in Table A below.

TABLE A

| Sample No. | Coupler | Color Hue (Y/C) | Variation in Color Density due to fluctuation of composition of blix solution used | Image Fastness 100° C. | 80° C., 70% RH | Color Fog | Remarks |
|---|---|---|---|---|---|---|---|
| 101 | comparative compound (1)* | 0.180 | 11 | 76 | 73 | 0.140 | comparative sample |
| 102 | comparative compound (2)* | 0.180 | 10 | 76 | 73 | 0.140 | comparative sample |
| 103 | comparative compound (3)* | 0.180 | 10 | 76 | 73 | 0.100 | comparative sample |
| 104 | comparative compound (4)* | 0.180 | 11 | 76 | 73 | 0.100 | comparative sample |
| 105 | comparative compound (5)* | 0.290 | 2 | 75 | 76 | 0.090 | comparative sample |
| 106 | compound (53) | 0.175 | 1 | 81 | 80 | 0.100 | sample of the invention |
| 107 | compound (54) | 0.170 | 1 | 90 | 89 | 0.090 | sample of the invention |
| 108 | compound (4) | 0.170 | 1 | 90 | 90 | 0.088 | sample of the invention |
| 109 | compound (1) | 0.170 | 0 | 90 | 90 | 0.088 | sample of the invention |
| 110 | compound (7) | 0.170 | 1 | 90 | 90 | 0.090 | sample of the invention |
| 111 | compound (8) | 0.170 | 1 | 91 | 90 | 0.090 | sample of the invention |
| 112 | compound (18) | 0.170 | 0 | 91 | 90 | 0.090 | sample of the invention |
| 113 | compound (22) | 0.170 | 1 | 90 | 90 | 0.090 | sample of the invention |
| 114 | compound (23) | 0.170 | 1 | 90 | 90 | 0.090 | sample of the invention |
| 115 | compound (38) | 0.170 | 1 | 90 | 90 | 0.090 | sample of the invention |

The comparative compounds used above are mentioned below.

*Comparative Compound (1):

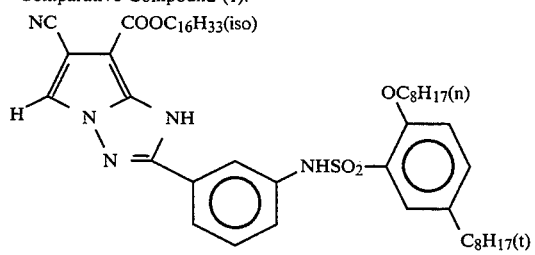

*Comparative Compound (2):

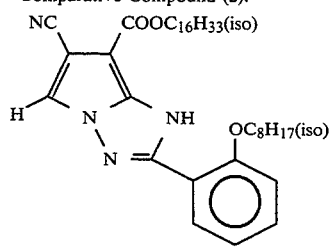

*Comparative Compound (3):

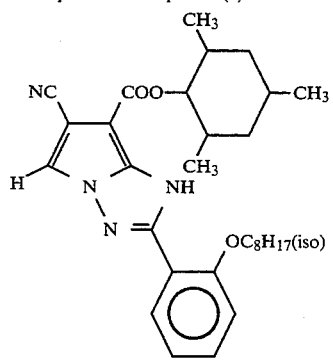

*Comparative Compound (4):

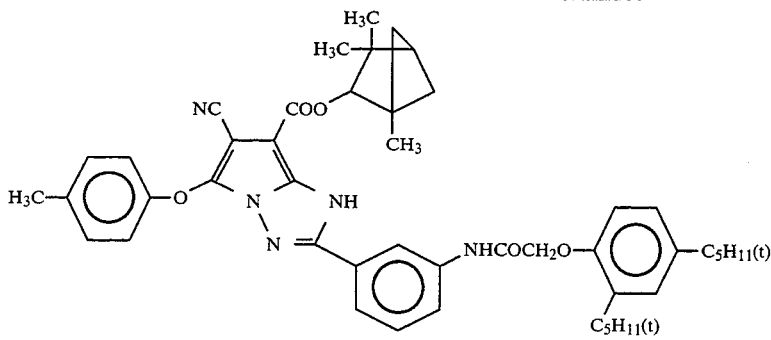

*Comparative Compound (5):

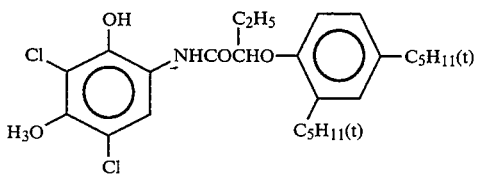

In view of the chemical equivalency of the coupler used and of the molar extinction coefficient of the dye to be formed, the amount of silver in the fifth layer in sample Nos. 101, 102, 105, 106 and 107 was 1.5 times the same in the fifth layer in sample No. 108, and the amount of the coupler in the fifth layer in sample No. 105 was 2 times the same in the fifth layer in sample No. 108. In the other samples, the amount of the coupler in the fifth layer was the same molar amount of the coupler in sample No. 108.

From Table A, it is noted that the samples of the present invention gave color images having excellent color hue and image fastness but having reduced cyan color fog. It is also noted therefrom that the samples of the present invention containing a cyan coupler having a split-off group at its 5-position are better than the others.

EXAMPLE 2

The first to twelfth layers mentioned below were coated on a 220 μm-thick paper support, of which the both surfaces had been laminated with polyethylene, to for a color photographic material (sample No. 208). The polyethylene below the first layer on the support contained 15% by weight of anatase-type titanium oxide as a white pigment, along with a small amount of ultramarine as a bluish dye. The chromaticity of the surface of the support was comprised of 89.0, −0.18 and −0.73, respectively, when represented by the trichromatic system (L*, a*, b*).

Layer Constitution

Compositions of the layers of constituting sample No. 208 are mentioned below, in which the numerical value indicates the amount coated (g/m$^2$) and the amount of the silver halide coated is represented as silver therein.

| First Layer: Gelatin Layer | |
|---|---|
| Gelatin | 0.30 |
| Second Layer: Anti-halation Layer | |
| Black Colloidal Silver | 0.07 |
| Gelatin | 0.50 |
| Third Layer: Low-sensitivity Red-sensitive Layer | |
| Silver Chloroiodobromide Emulsion color-sensitized with red-sensitizing dyes (ExS-1, 2, 3) (I-in-core type, cubic core/shell grains, having a silver chloride content of 1 mol %, a silver iodide content of 4 mol %, a mean grain size of 0.3 μm and a grain size distribution of 10%) | 0.03 |
| Silver Iodobromide Emulsion color-sensitized with red-sensitizing dyes (ExS-1, 2, 3) (cubic grains, having a silver iodide content of 4 mol %, a mean grain size of 0.5 μm and a grain size distribution of 15%) | 0.03 |
| Gelatin | 1.00 |
| Cyan Coupler (Compound (1) mentioned above) | 0.08 |
| Anti-fading Agent (1/1/1 mixture of Cpd-2′, 3′, 4′) | 0.12 |
| Coupler Dispersing Medium (Cpd-6′) | 0.03 |
| Coupler Solvent (1/1/1 mixture of Solv-1′, 2′, 3′) | 0.06 |
| Development Accelerator (Cpd-13′) | 0.05 |
| Fourth Layer: High-sensitivity Red-sensitive Layer | |
| Silver Iodobromide Emulsion color-sensitized with red-sensitizing dyes (ExS-1, 2, 3) (I-in-core type, tabular grains, having an aspect ratio of 8, a silver iodide content of 6 mol %, a mean grain size of 0.8 μm and a grain size distribution of 20%) | 0.07 |
| Gelatin | 1.00 |
| Cyan Coupler (Compound (1) mentioned above) | 0.12 |
| Anti-fading Agent (1/1/1 mixture of Cpd-2′, 3′, 4′) | 0.15 |
| Coupler Dispersing Medium (Cpd-6′) | 0.03 |
| Coupler Solvent (1/1/1 mixture of Solv-1′, 2′, 3′) | 0.10 |
| Fifth Layer: Interlayer | |
| Magenta Colloidal Silver | 0.02 |
| Gelatin | 1.00 |
| Color Mixing Preventing Agent (Cpd-7′, 16′) | 0.08 |
| Solvent for Color Mixing Preventing Agent (Solv-4′, 5′) | 0.16 |
| Polymer Latex (Cpd-8) | 0.10 |
| Sixth Layer: Low-sensitivity Green-sensitive Layer | |
| Silver Chloroiodobromide Emulsion color-sensitized with green-sensitizing dye (ExS-4) (I-in-core type, cubic core/shell grains, having a silver chloride content of 1 mol %, a silver iodide content of 2.5 mol %, a mean grain size of 0.28 μm and a grain size distribution of 8%) | 0.04 |
| Silver Iodobromide Emulsion color-sensitized with green-sensitizing dye (ExS-4) (cubic grains, having a silver iodide content of 2.5 mol %, a mean grain size of 0.48 μm and a grain size distribution of 12%) | 0.06 |
| Gelatin | 0.80 |
| Magenta Coupler (1/1 mixture of ExM-1, 2) | 0.10 |
| Anti-fading Agent (Cpd-9′) | 0.10 |
| Anti-staining Agent (1/1 mixture of Cpd-10′, 11′) | 0.01 |
| Anti-staining Agent (Cpd-5′) | 0.001 |

| | |
|---|---|
| Anti-staining Agent (Cpd-12') | 0.01 |
| Coupler Dispersing Medium (Cpd-6') | 0.05 |
| Coupler Solvent (Solv-4', 6') | 0.15 |
| Seventh Layer: High-sensitivity Green-sensitive Layer | |
| Silver Iodobromide Emulsion color-sensitized with green-sensitizing dye (ExS-4) (even-core type, tabular grains, having an aspect ratio of 9, a silver iodide content of 3.5 mol %, a mean grain size of 1.0 μm and a grain size distribution of 21%) | 0.10 |
| Gelatin | 0.80 |
| Magenta Coupler (1/1 mixture of ExM-1, 2) | 0.10 |
| Anti-fading Agent (Cpd-9') | 0.10 |
| Anti-staining Agent (1/1 mixture of Cpd-10, 11) | 0.01 |
| Anti-staining Agent (Cpd-5') | 0.001 |
| Anti-staining Agent (Cpd-12') | 0.01 |
| Coupler Dispersing Medium (Cpd-6') | 0.05 |
| Coupler Solvent (Solv-4', 6') | 0.15 |
| Eighth Layer: Yellow Filter Layer | |
| Yellow Colloidal Silver | 0.14 |
| Gelatin | 1.00 |
| Color Mixing Preventing Agent (Cpd-7') | 0.06 |
| Solvent for Color Mixing Preventing Agent (Solv-4', 5') | 0.15 |
| Polymer Latex (Cpd-8') | 0.10 |
| Ninth Layer: Low-sensitivity Blue-sensitive Layer | |
| Silver Chloroiodobromide Emulsion color-sensitized with blue-sensitizing dyes (ExS-5, 6) (I-in-core type, cubic core/shell grains, having a silver chloride content of 2 mol %, a silver iodide content of 2.5 mol %, a mean grain size of 0.38 μm and a grain size distribution of 8%) | 0.07 |
| Silver Iodobromide Emulsion color-sensitized with blue-sensitizing dyes (ExS-5, 6) (cubic grains, having a silver iodide content of 2.5 mol %, a mean grain size of 0.55 μm and a grain size distribution of 11%) | 0.10 |
| Gelatin | 0.50 |
| Yellow Coupler (1/1 mixture of ExY-1, 2) | 0.20 |
| Anti-staining Agent (Cpd-5') | 0.001 |
| Anti-fading Agent (Cpd-14') | 0.10 |
| Coupler Dispersing Medium (Cpd-6') | 0.05 |
| Coupler Solvent (Solv-2') | 0.05 |
| Tenth Layer: High-sensitivity Blue-sensitive Layer | |
| Silver Iodobromide Emulsion color-sensitized with blue-sensitizing dyes (ExS-5, 6) (tabular grains, having an aspect ratio of 14, a silver iodide content of 2.5 mol %, a mean grain size of 1.4 μm and a grain size distribution of 21%) | 0.25 |
| Gelatin | 1.00 |
| Yellow Coupler (1/1 mixture of ExY-1, 2) | 0.40 |
| Anti-staining Agent (Cpd-5') | 0.002 |
| Anti-fading Agent (Cpd-14') | 0.10 |
| Coupler Dispersing Medium (Cpd-6') | 0.15 |
| Coupler Solvent (Solv-2') | 0.10 |
| Eleventh Layer: Ultraviolet Absorbing Layer | |
| Gelatin | 1.50 |
| Ultraviolet Absorbent (1/1/1/1 mixture of Cpd-1', 2', 4', 15') | 1.00 |
| Color Mixing Preventing Agent (Cpd-7', 16') | 0.06 |
| Dispersing Medium (Cpd-6') | 0.30 |
| Ultraviolet Absorbent Solvent (Solv-1', 2') | 0.15 |
| Anti-irradiation Dye (Cpd-17', 18') | 0.02 |
| Anti-irradiation Dye (Cpd-19', 20') | 0.02 |
| Twelfth Layer: Protective Layer | |
| Fine Silver Chlorobromide Grains (having a silver chloride content of 97 mol % and a mean grain size of 0.2 μm) | 0.07 |
| Modified Poval | 0.02 |
| Gelatin | 1.50 |
| Gelatin Hardening Agent (1/1 mixture of H-1, 2) | 0.17 |

The layers each contained Alkanol XC (made by Du Pont Co.) and sodium alkylbenzenesulfonate as emulsification and dispersion aids, succinate and Magefac F-120 (made by Dai-Nippon Ink Co.) as coating aids and Cpd-24', 25' and 26' as antiseptics, in addition to the above-mentioned components. The silver halide layers and the colloidal silver-containing layers each contained Cpd-21', 22' and 23' as stabilizers. The compounds used in this example are shown below.

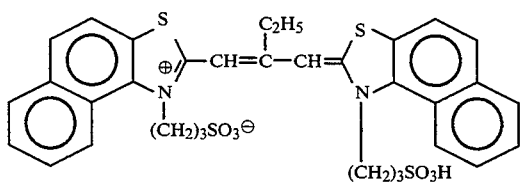 ExS-1

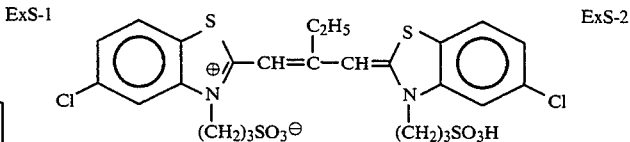 ExS-2

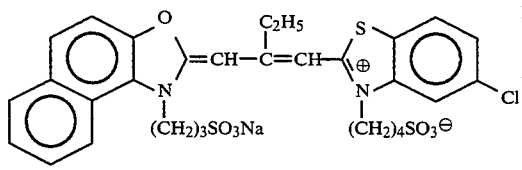 ExS-3

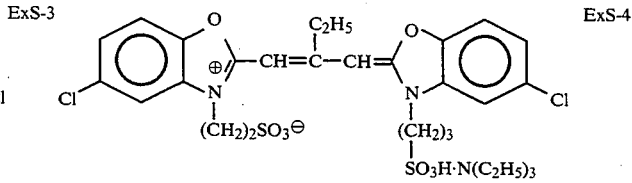 ExS-4

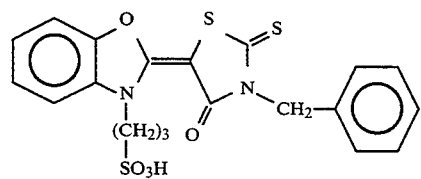 ExS-5

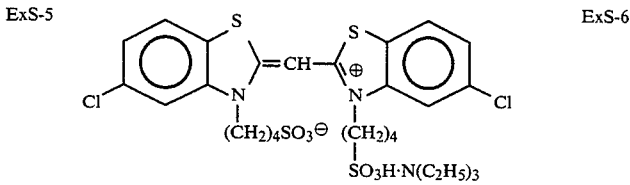 ExS-6

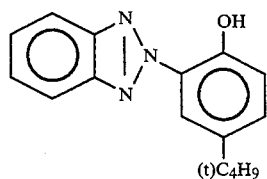 Cpd-1'

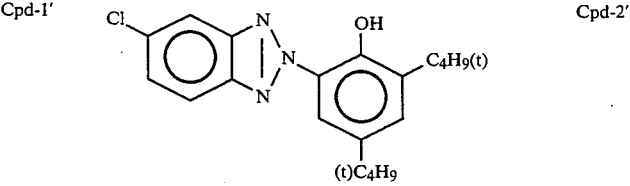 Cpd-2'

-continued
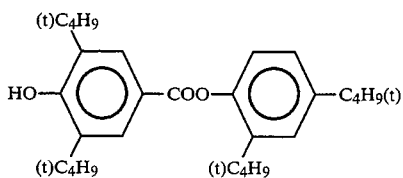
Cpd-3'
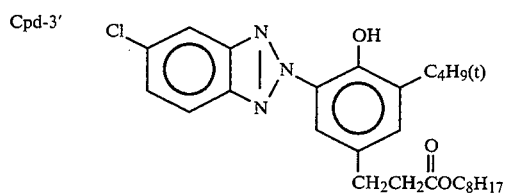
Cpd-4'
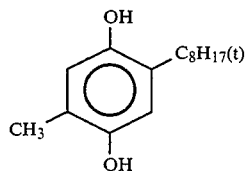
Cpd-5'
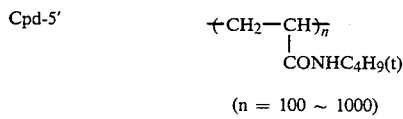
Cpd-6'
(n = 100 ~ 1000)
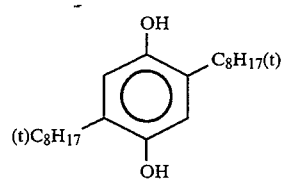
Cpd-7'
Polyethyl Acrylate
(Mw = 10,000 ~ 100,000)
Cpd-8'
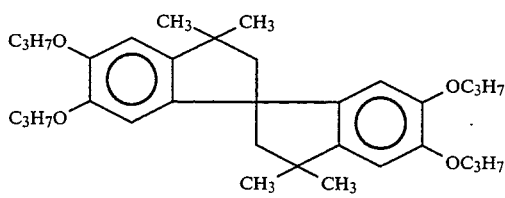
Cpd-9'
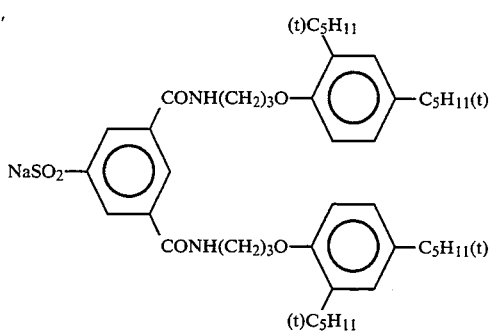
Cpd-10'
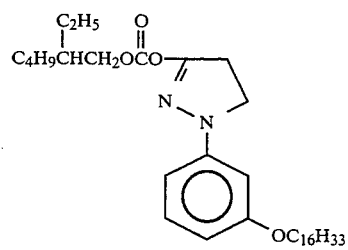
Cpd-11'
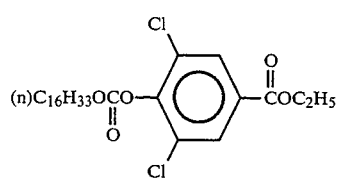
Cpd-12'
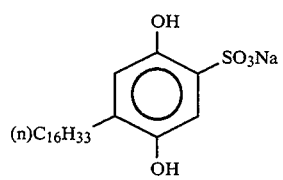
Cpd-13'
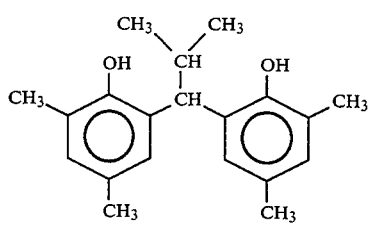
Cpd-14'
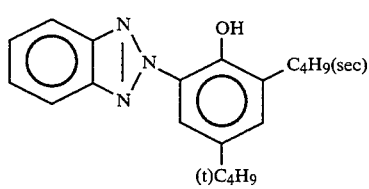
Cpd-15'
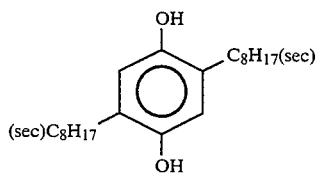
Cpd-16'

-continued
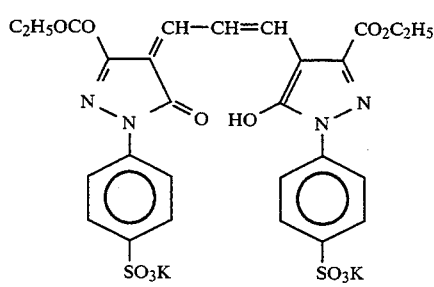
Cpd-17'
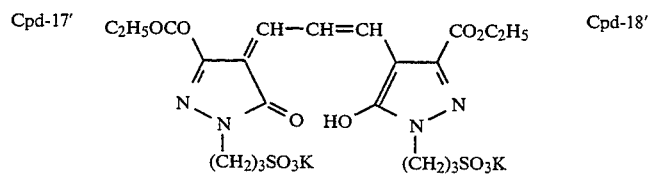
Cpd-18'
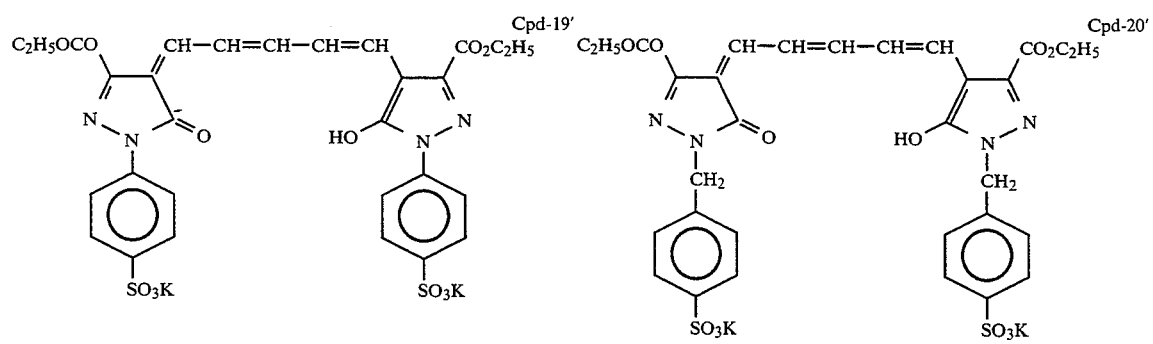
Cpd-19'    Cpd-20'
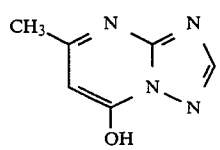
Cpd-21'
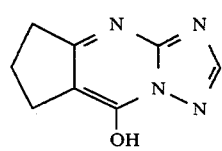
Cpd-22'
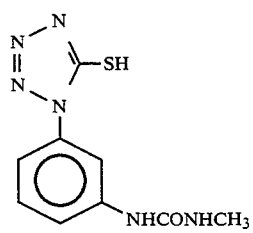
Cpd-23'
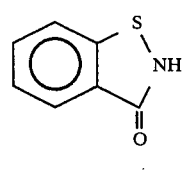
Cpd-24'
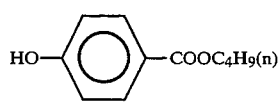
Cpd-25'
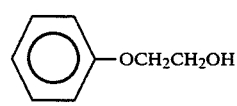
Cpd-26'
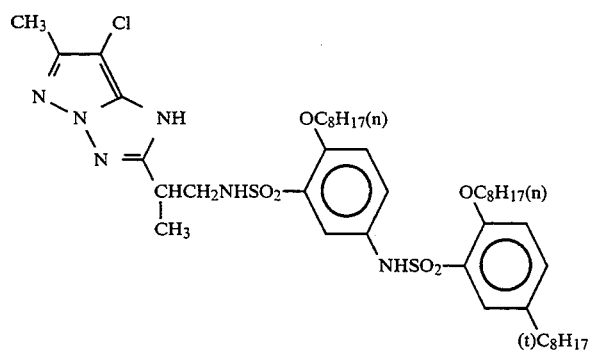
ExM-1

ExM-2

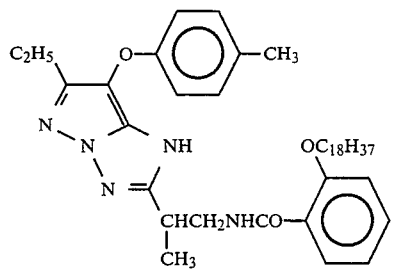

ExY-1

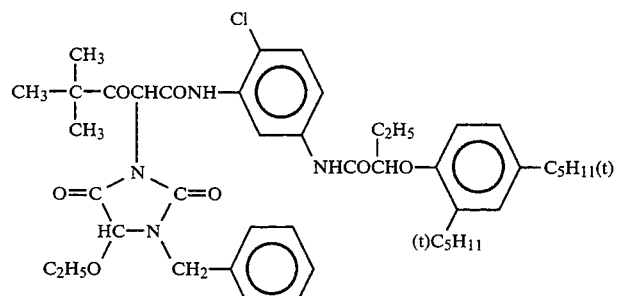

ExY-2

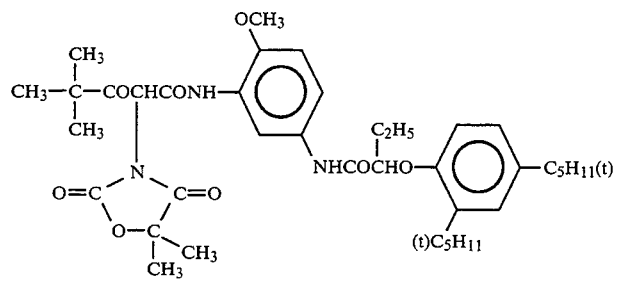

Solv-1'
  Di(2-ethylhexyl) Phthalate
Solv-2'
  Trinonyl Phosphate
Solv-3'
  Di(3-methylhexyl) Phthalate
Solv-4'
  Tricresyl Phosphate
Solv-5'
  Dibutyl Phthalate
Solv-6'
  Trioctyl Phosphate
H-1
  1,2-Bis(vinylsulfonylacetamido)ethane
H-2
  4,6-Dichloro-2-hydroxy-1,3,5-triazine Sodium Salt Sample Nos. 201 to 207 and 209 to 214 were prepared in the same manner as in preparation of sample No. 208, except that the cyan coupler in the third layer and the fourth layer was changed to that indicated in Table B below.

TABLE B

| Sample No. | Cyan Coupler | Remarks |
|---|---|---|
| 201 | comparative compound (1)* | comparative sample |
| 202 | comparative compound (2)* | comparative sample |
| 203 | comparative compound (3)* | comparative sample |
| 204 | comparative compound (4)* | comparative sample |
| 205 | compound (53) | sample of the invention |
| 206 | compound (54) | sample of the invention |
| 207 | compound (4) | sample of the invention |
| 208 | compound (1) | sample of the invention |
| 209 | compound (7) | sample of the invention |

TABLE B-continued

| Sample No. | Cyan Coupler | Remarks |
|---|---|---|
| 210 | compound (8) | sample of the invention |
| 211 | compound (18) | sample of the invention |
| 212 | compound (22) | sample of the invention |
| 213 | compound (23) | sample of the invention |
| 214 | compound (38) | sample of the invention |

The comparative compounds used above are mentioned below.

*Comparative Compound (1):

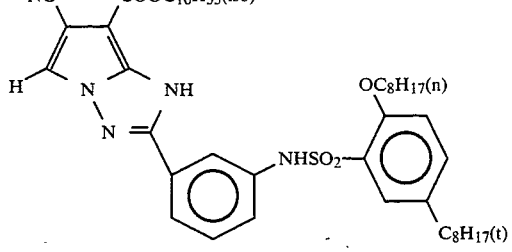

*Comparative Compound (2):

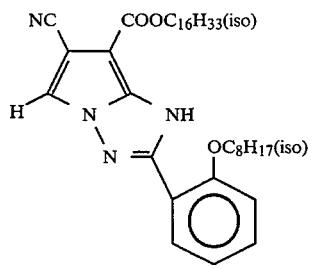

*Comparative Compound (3):

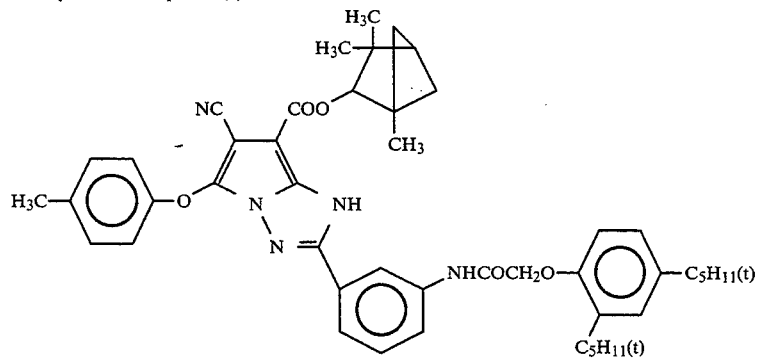

*Comparative Compound (4):
1/1 (by mol) mixture of the following compounds:

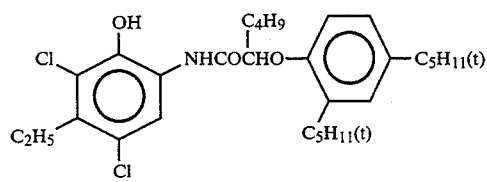

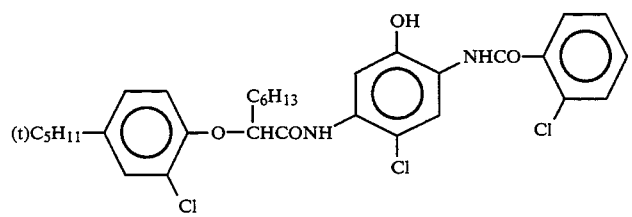

In view of the chemical equivalency of the coupler used and of the molar extinction coefficient of the dye to be formed, the amounts of silver in the third and fourth layers in sample Nos. 201, 202, 204, 205 and 206 were 1.5 times the same in those layers in sample No. 208, and the amounts of the coupler in the third and fourth layers in sample No. 204 were 2 times the same in those layers in sample No. 208. In the other samples, the amounts of the coupler in the third and fourth layers was the same molar amount of the coupler in sample No. 208.

The thus-prepared silver halide color photographic material, sample No. 208 was exposed to such a degree that about 30% of the coated silver is developed to give gray color. The exposed sample No. 208 was processed in accordance with the process mentioned below, using an automatic developing machine, until the total amount of the replenisher to the machine became 3 times the tank capacity.

| Processing Step | Process: Temperature | Time | Tank Capacity | Amount of Replenisher |
|---|---|---|---|---|
| First Development | 75 sec | 38° C. | 8 liters | 330 ml/m² |
| First Rinsing (1) | 45 sec | 33° C. | 5 liters | — |
| First Rinsing (2) | 45 sec | 33° C. | 5 liters | 5000 ml/m² |
| Reversal Exposure | 15 sec | 100 lux | | |
| Color Development | 135 sec | 38° C. | 15 liters | 330 ml/m² |
| Second Rinsing | 45 sec | 33° C. | 5 liters | 1000 ml/m² |
| Blix (1) | 60 sec | 38° C. | 7 liters | — |
| Blix (2) | 60 sec | 38° C. | 7 liters | 220 ml/m² |
| Third Rinsing (1) | 45 sec | 33° C. | 5 liters | — |
| Third Rinsing (2) | 45 sec | 33° C. | 5 liters | — |
| Third Rinsing (3) | 45 sec | 33° C. | 5 liters | 5000 ml/m² |

-continued

| Processing Step | Process: Temperature | Time | Tank Capacity | Amount of Replenisher |
|---|---|---|---|---|
| Drying | 45 sec | 75° C. | | |

The first rinsing and the third rinsing each were effected by countercurrent cascade system. Preferably, a rinsing water was applied to the first rinsing tank (2), while the overflow therefrom was led to the first rinsing tank (1). In the same way, a rinsing water was applied to the third rinsing tank (3), while the overflow therefrom was led to the third rinsing tank (2) and the overflow therefrom to the third rinsing tank (1).

Compositions of the processing solutions used above are mentioned below.

| First Developer | Tank Solution | Replenisher |
|---|---|---|
| Pentasodium Nitrilo-N,N,N-trimethylenephosphonate | 1.0 g | 1.0 g |
| Pentasodium Diethylenetriamine-pentaacetate | 3.0 g | 3.0 g |
| Potassium Sulfite | 30.0 g | 30.0 g |
| Potassium Thiocyanate | 1.2 g | 1.2 g |
| Potassium Carbonate | 35.0 g | 35.0 g |
| Potassium Hydroquinone-monosulfonate | 25.0 g | 25.0 g |
| 1-Phenyl-4-hydroxymethyl-4-methyl-3-pyrazolidone | 2.0 g | 2.0 g |
| Potassium Bromide | 0.5 g | — |
| Potassium Iodide | 5.0 mg | — |
| Water to make | 1000 ml | 1000 ml |
| pH (adjusted with HCl or KOH) | 9.60 | 9.70 |

| Color Developer | Tank Solution | Replenisher |
|---|---|---|
| Benzyl Alcohol | 15.0 ml | 15.0 ml |
| Diethylene Glycol | 12.0 ml | 14.0 ml |
| 3,6-Dithia-1,8-octanediol | 0.20 g | 0.25 g |
| Pentasodium Nitrilo-N,N,N-trimethylenephosphonate | 0.5 g | 0.5 g |
| Pentasodium Diethylenetriamine-pentaacetate | 2.0 g | 2.0 g |
| Sodium Sulfite | 2.0 g | 2.5 g |
| Hydroxylamine Sulfate | 3.0 g | 3.6 g |
| N-ethyl-N-(β-methanesulfon-amidoethyl)-3-methyl-4-amino-aniline.3/2 Sulfate.Monohydrate | 5.0 g | 8.0 g |
| Brightening Agent (diaminostilbene compound) | 1.0 g | 1.2 g |
| Potassium Bromide | 0.5 g | — |
| Potassium Iodide | 1.0 mg | — |
| Water to make | 1000 ml | 1000 ml |
| pH (adjusted with HCl or KOH) | 10.25 | 10.40 |

| Blix Solution (tank solution and replenisher were the same) | Tank Solution |
|---|---|
| Disodium Ethylenediamine-tetraacetate Dihydrate | 5.0 g |
| Ammonium Ethylenediamine-tetraacetato/Fe(III) Monohydrate | 80.0 g |
| Sodium Sulfite | 15.0 g |
| Ammonium Thiosulfate (750 g/liter) | 150 ml |
| 2-Mercapto-1,3,4-triazole | 0.5 g |
| Water to make | 1000 ml |
| pH (adjusted with acetic acid or aqueous ammonia) | 6.50 |

Sample Nos. 201 to 214 were exposed in the same manner as in Example 1 and then processed also in the same manner as in Example 1, using the running solutions that had been prepared by the above-mentioned continuous-processing. The processed samples were evaluated in the same manner as in Example 1. The test results showed that the color hue and the image fastness of the color images formed in the samples of the present invention are excellent while the cyan color fog in the processed samples of the present invention is little.

EXAMPLE 3

Sample Nos. 301 to 314 were prepared in the same manner as in preparation of sample No. 101 in Example 1 in JP-A-5-134351, except that the cyan coupler in the third layer was changed to that indicated in Table C below.

These samples were processed in the same manner as in Examples 1 and 2 in JP-A-5-134351.

The processed samples were evaluated with respect to the color hue and the image fastness of the images formed and also to the cyan fog in the unexposed area. The test results showed that the samples containing the cyan coupler of the present invention were superior to those containing the comparative coupler.

TABLE C

| Sample No. | Cyan Coupler | Remarks |
|---|---|---|
| 301 | comparative compound (1)* | comparative sample |
| 302 | comparative compound (2)* | comparative sample |
| 303 | comparative compound (3)* | comparative sample |
| 304 | comparative compound (4)* | comparative sample |
| 305 | compound (53) | sample of the invention |
| 306 | compound (54) | sample of the invention |
| 307 | compound (4) | sample of the invention |
| 308 | compound (1) | sample of the invention |
| 309 | compound (7) | sample of the invention |
| 310 | compound (8) | sample of the invention |
| 311 | compound (18) | sample of the invention |
| 312 | compound (22) | sample of the invention |
| 313 | compound (23) | sample of the invention |
| 314 | compound (55) | sample of the invention |

The comparative compounds used above are mentioned below.

*Comparative Compound (1):

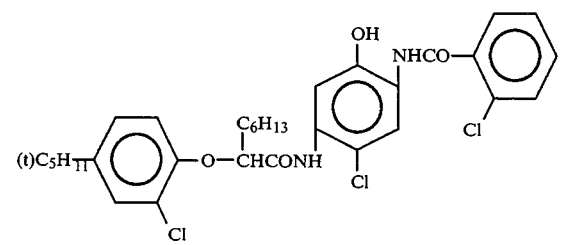

*Comparative Compound (2):

-continued

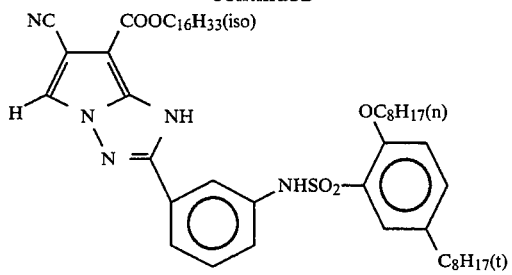

*Comparative Compound (3):

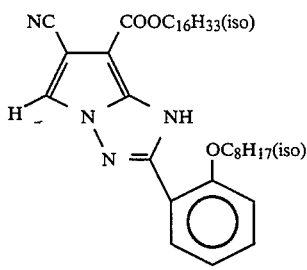

*Comparative Compound (4):

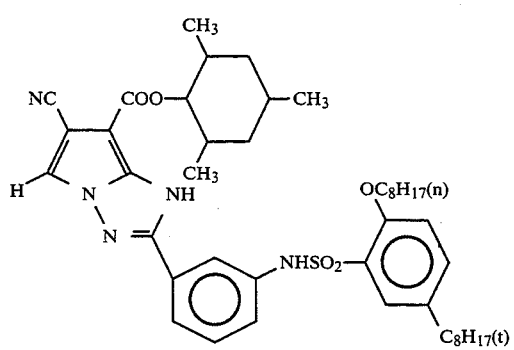

In view of the chemical equivalency of the coupler used and of the molar extinction coefficient of the dye to be formed, the amount of silver in the third layer in sample Nos. 308 to 314 was 1/1.5 times the same in the third layer in sample No. 301, and the amount of the coupler in the third layer in sample Nos. 302 to 314 was 2 times the same in the third layer in sample No. 301.
Advantage of the invention According to the present invention, obtained is a color photographic material capable of forming a color image having excellent color hue and color fastness. The color fog in the unexposed area of the material is little.

While the invention has been described in detail and with reference to specific embodiments thereof, it will be apparent to one skilled in the art that various changes and modifications can be made therein without depanting from the sprit and scope thereof.

What is claimed is:

1. A silver halide color photographic material comprising a support having provided thereon at least one layer containing at least one cyan coupler represented by formula (I)

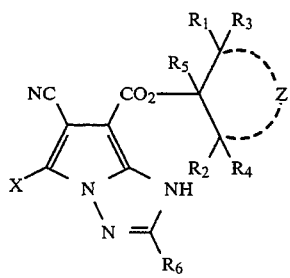

wherein
$R_1$ and $R_2$ each represent a substituent except methyl group;
$R_3$, $R_4$, $R_5$ and $R_6$ each represent a hydrogen atom or a substituent;
Z represents a non-metallic atom or a non-metallic atomic group necessary for forming a ring and the non-metallic atomic group off Z may optionally be substituted by substituent(s); and
X represents a hydrogen atom, or a group of splitting off from the formula by coupling reaction with an oxidation product of an aromatic primary amine color developing agent.

2. The silver halide color photographic material as in claim 1, wherein $R_1$ and $R_2$ each represents a halogen atom, an aliphatic group having from 2 to 30 carbon atoms, an aryl group, a heterocyclic group, an alkoxy group, an aryloxy group, a heterocyclic-oxy group, an alkyl-, aryl- or heterocyclic-thio group, an alkyl-, aryl- or heterocylic-acyloxy group, a carbamoyloxy group, a silyloxy group, an alkyl- aryl- or heterocyclic-sulfonyloxy group, an acylamino group, an alkylamino group, an arylamino group, an ureido group, a sulfamoylamino group, an alkenyloxy group, a formyl group, an alkyl-, aryl- or heterocyclic-acyl group, an alkyl-, aryl- or heterocyclic-sulfonyl group, an alkyl-, aryl- or heterocyclic-sulfinyl group, an alkyl-, aryl- or heterocyclic-oxycarbonyl group, an alkyl-, aryl- or heterocyclic-oxycarbonylamino group, an alkyl-, aryl- or heterocyclic-sulfonamide group, a carbamoyl group, a sulfamoyl group, a phosphonyl group, a sulfamido group, an imido group, an azolyl group, an alkyl- or aryl-substituted silyl group, a hydroxyl group, a cyano group, a carboxyl group, a nitro group, a sulfo group, or an unsubstituted amino group.

3. The silver halide color photographic material as in claim 1, wherein $R_1$ and $R_2$ each represents an aliphatic group having from 2 to 30 carbon atoms, an aryl group having from 6 to 30 carbon atoms, an alkoxy group having from 1 to 30 carbon atoms, an aryloxy group having from 6 to 30 carbon atoms, a halogen atom, an alkyl- or aryl-oxycarbonyl group, a carbamoyl group, or an alkyl- or aryl-substituted silyl group.

4. The silver halide color photographic material as in claim 1, wherein $R_1$ and $R_2$ each represents a branched alkyl group having from 3 to 30 carbon atoms.

5. The silver halide color photographic material as in claim 1, wherein $R_3$, $R_4$, $R_5$ and $R_6$ each represents a hydrogen atom, a halogen atom, an aliphatic group, an aryl group, a heterocyclic group, an alkoxy group, an aryloxy group, a heterocyclic-oxy group, an alkyl-, aryl- or heterocyclic-thio group, an alkyl-, aryl- or heterocyclic-acyloxy group, a carbamoyloxy group, a silyloxy group, an alkyl- aryl- or heterocyclic-sulfonyloxy group, an acylamino group, an alkylamino group, an arylamino group, an ureido group, a sulfamoylamino group, an alkenyloxy group, a formyl group, an alkyl-, aryl- or heterocyclic-acyl group, an alkyl-, aryl- or heterocyclic-sulfonyl group, an alkyl-, aryl- or heterocyclic-sulfinyl group, an alkyl-, aryl- or heterocyclic-oxycarbonyl group, an alkyl-, aryl- or heterocyclic-oxycarbonylamino group, an alkyl-, aryl- or heterocyclic-sulfonamide group, a carbamoyl group, a sulfamoyl group, a phosphonyl group, a sulfamido group, an imido group, an azolyl group, an alkyl- or aryl-substituted silyl group, a hydroxyl group, a cyano group, a carboxyl group, a nitro group, a sulfo group, or an unsubstituted amino group.

6. The silver halide color photographic material as in claim 5, wherein $R_6$ is represented by

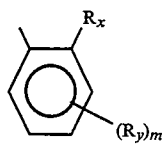

wherein Rx and Ry each represents a substituent and m represents an integer of from 0 to 4.

7. The silver halide color photographic material as in claim 6, wherein Rx is an alkoxy group having from 1 to 40 carbon atoms, or an aryloxy group having from 6 to 46 carbon atoms.

8. The silver halide color photographic material as in claim 1, wherein $R_3$, $R_4$, and $R_5$ each represents a hydrogen atom, an alkyl group having from 1 to 30 carbon atoms, an aryl group, an alkoxy group, an aryloxy group, a halogen atom, or a group that is bonded to the formula via an ester group, an amido group or a silicon atom.

9. The silver halide color photographic material as in claim 1, wherein $R_3$, $R_4$, and $R_5$ each represents a hydrogen atom.

10. The silver halide color photographic material as in claim 1, wherein $R_6$ is an alkyl group, an aryl group, a heterocyclic group, a carbamoyl group, an acylamino group, or an ureido group.

11. The silver halide color photographic material as in claim 1, wherein Z represents an atom or an atomic group necessary for forming a 5-, 6-, 7- or 8-membered ring.

12. The silver halide color photographic material as in claim 1, wherein Z represents a divalent amino group, an ether bond, a thioether bond, an alkylene group, an alkenylene group, an imino group, a sulfonyl group, or a carbonyl group.

13. The silver halide color photographic material as in claim 1, wherein Z represents an alkylene group or an alkenylene group.

14. The silver halide color photographic material as in claim 1, wherein Z represents an alkylene group.

15. The silver halide color photographic material as in claim 1, wherein the moiety of

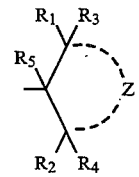

is represented by

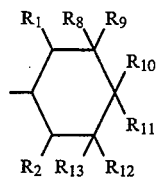

wherein $R_8$ to $R_{13}$ each represents a hydrogen atom or a substituent.

16. The silver halide color photographic material as in claim 1, wherein X represents a hydrogen atom, a halogen atom, an alkoxy group, an aryloxy group, a heterocyclic-oxy group, an alkyl-, aryl- or heterocyclicacyl-oxy group, an alkyl-, aryl- or heterocyclic-sulfonyloxy group, a dialkyl- or diaryl-phosphonoxy group, a dialkyl- or diaryl-phosphinoxy group, an alkoxycarbonyloxy group, an aryloxycarbonyloxy group, a heterocyclic-oxycarbonyloxy group, an alkyl-, aryl- or heterocyclic-sulfonyl group, an alkyl-, aryl- or heterocyclic-sulfinyl group, an alkyl-, aryl- or heterocyclic-carbonyl group, an alkyl-, aryl- or heterocyclic-acylamino group, an alkyl-, aryl- or heterocyclic-sulfonamido group, a carbamoylamino group, an alkyl-, aryl- or heterocyclic-thio group, an imido group, an arylazo group, and a 5-membered or 6-membered, nitrogen-containing heterocyclic group that bonds to the coupling position of the formula via its nitrogen atom.

17. The silver halide color photographic material as in claim 1, wherein X is a chlorine atom.

18. The silver halide color photographic material as in claim 1, wherein said cyan coupler is incorporated into a red-sensitive silver halide emulsion layer.

19. The silver halide color photographic material as in claim 1, wherein the content of said cyan coupler is from $1 \times 10^{-3}$ mol to 1 mol per mol of the silver halide in the layer containing said cyan coupler.

* * * * *